(12) United States Patent
Bolam

(10) Patent No.: US 8,035,376 B2
(45) Date of Patent: Oct. 11, 2011

(54) OPTICAL PUMPING MODULES, POLARIZED GAS BLENDING AND DISPENSING SYSTEMS, AND AUTOMATED POLARIZED GAS DISTRIBUTION SYSTEMS AND RELATED DEVICES AND METHODS

(75) Inventor: Kenneth Bolam, Raleigh, NC (US)

(73) Assignee: Medi-Physics, Inc., Princeton, NJ (US)

( * ) Notice: Subject to any disclaimer, the term of this patent is extended or adjusted under 35 U.S.C. 154(b) by 537 days.

(21) Appl. No.: 11/856,963

(22) Filed: Sep. 18, 2007

(65) Prior Publication Data

US 2008/0006266 A1 Jan. 10, 2008

Related U.S. Application Data

(62) Division of application No. 10/277,909, filed on Oct. 22, 2002, now Pat. No. 7,287,390.

(60) Provisional application No. 60/335,706, filed on Oct. 22, 2001.

(51) Int. Cl.
*G01V 3/00* (2006.01)
(52) U.S. Cl. ...................................................... 324/304
(58) Field of Classification Search .......... 324/300–322; 600/410–435
See application file for complete search history.

(56) References Cited

U.S. PATENT DOCUMENTS

| 5,545,396 | A | | 8/1996 | Albert et al. |
| 5,642,625 | A | * | 7/1997 | Cates et al. ..................... 62/55.5 |
| 5,809,801 | A | | 9/1998 | Cates, Jr. et al. |
| 6,079,213 | A | | 6/2000 | Driehuys et al. |
| 6,199,385 | B1 | * | 3/2001 | Driehuys et al. ............... 62/51.1 |
| 6,237,363 | B1 | * | 5/2001 | Zollinger et al. ............... 62/600 |
| 6,286,319 | B1 | * | 9/2001 | Hasson et al. ................. 62/49.1 |
| 6,295,834 | B1 | * | 10/2001 | Driehuys ......................... 62/637 |
| 6,426,058 | B1 | * | 7/2002 | Pines et al. ..................... 424/9.3 |
| 6,427,452 | B2 | * | 8/2002 | Zollinger et al. ............... 62/51.1 |
| 6,430,960 | B1 | * | 8/2002 | Driehuys ......................... 62/637 |
| 6,484,532 | B2 | * | 11/2002 | Driehuys ......................... 62/637 |
| 6,523,356 | B2 | * | 2/2003 | Hasson et al. ................. 62/49.1 |
| 6,630,126 | B2 | | 10/2003 | Driehuys et al. |
| 6,818,202 | B2 | * | 11/2004 | Pines et al. ..................... 424/9.3 |
| 7,277,775 | B2 | * | 10/2007 | Teixeira ......................... 700/239 |
| 7,287,390 | B2 | * | 10/2007 | Bolam ............................ 62/55.5 |
| 7,287,391 | B2 | * | 10/2007 | Bolam ............................ 62/55.5 |
| 7,373,782 | B2 | * | 5/2008 | Driehuys et al. .............. 62/48.1 |
| 7,385,395 | B2 | * | 6/2008 | Pines et al. ..................... 324/301 |
| 2001/0029739 | A1 | | 10/2001 | Zollinger et al. |
| 2003/0108485 | A1 | | 6/2003 | Bolam |
| 2008/0006265 | A1 | * | 1/2008 | Bolam ........................ 128/200.24 |

* cited by examiner

*Primary Examiner* — Dixomara Vargas
(74) *Attorney, Agent, or Firm* — Robert F. Chisholm

(57) ABSTRACT

A method of providing polarized noble gas for NMR or MRI applications incorporates a control module, a plurality of optical pumping modules each including an optical pumping cell operably associated with the control module; a plurality of dispensing systems, one for each optical pumping module wherein each dispensing system is operably associated with the control module and the its associated optical pumping module to dispense meted volumes of polarized gas from the hyperpolarizer; the optical pumping modules, and the dispensing systems, where a noble gas is directed to a selected one of the optical pumping modules, polarized and dispensed by the associated dispensing system.

5 Claims, 22 Drawing Sheets

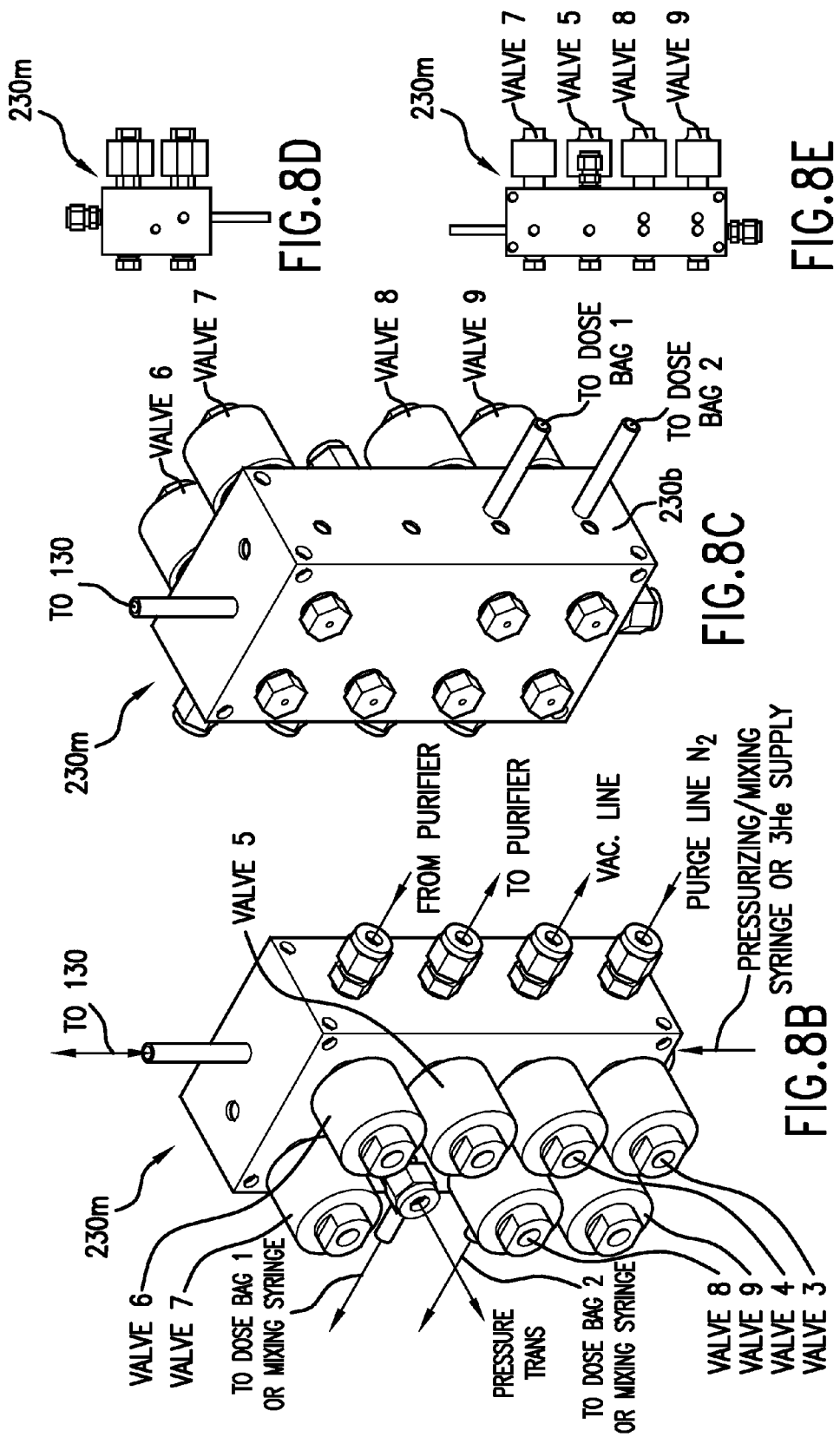

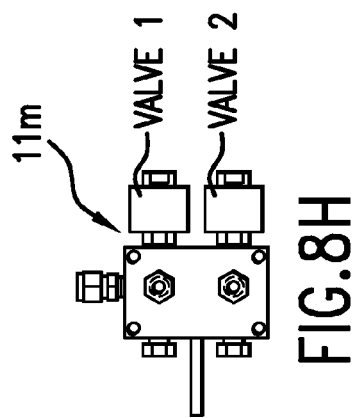
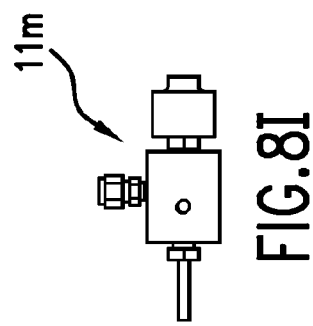
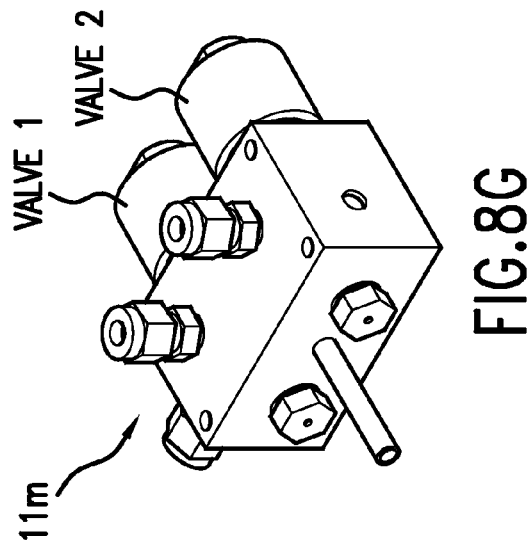
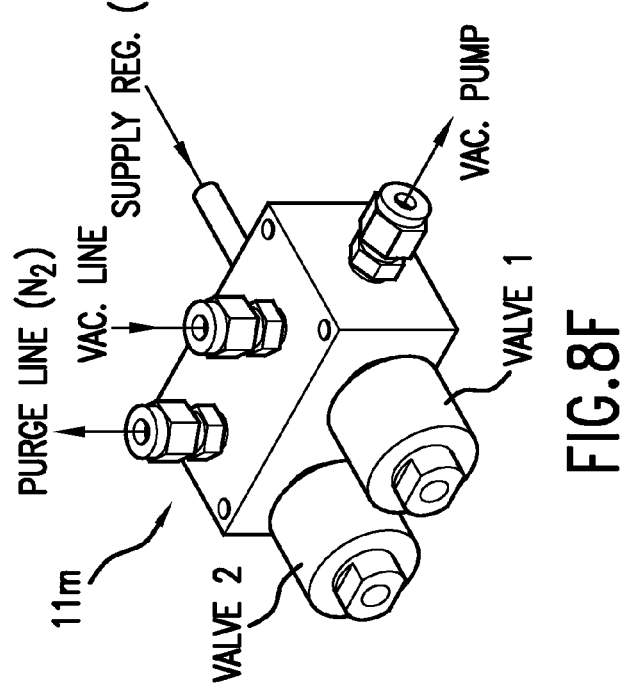
FIG.8H
FIG.8I
FIG.8G
FIG.8F

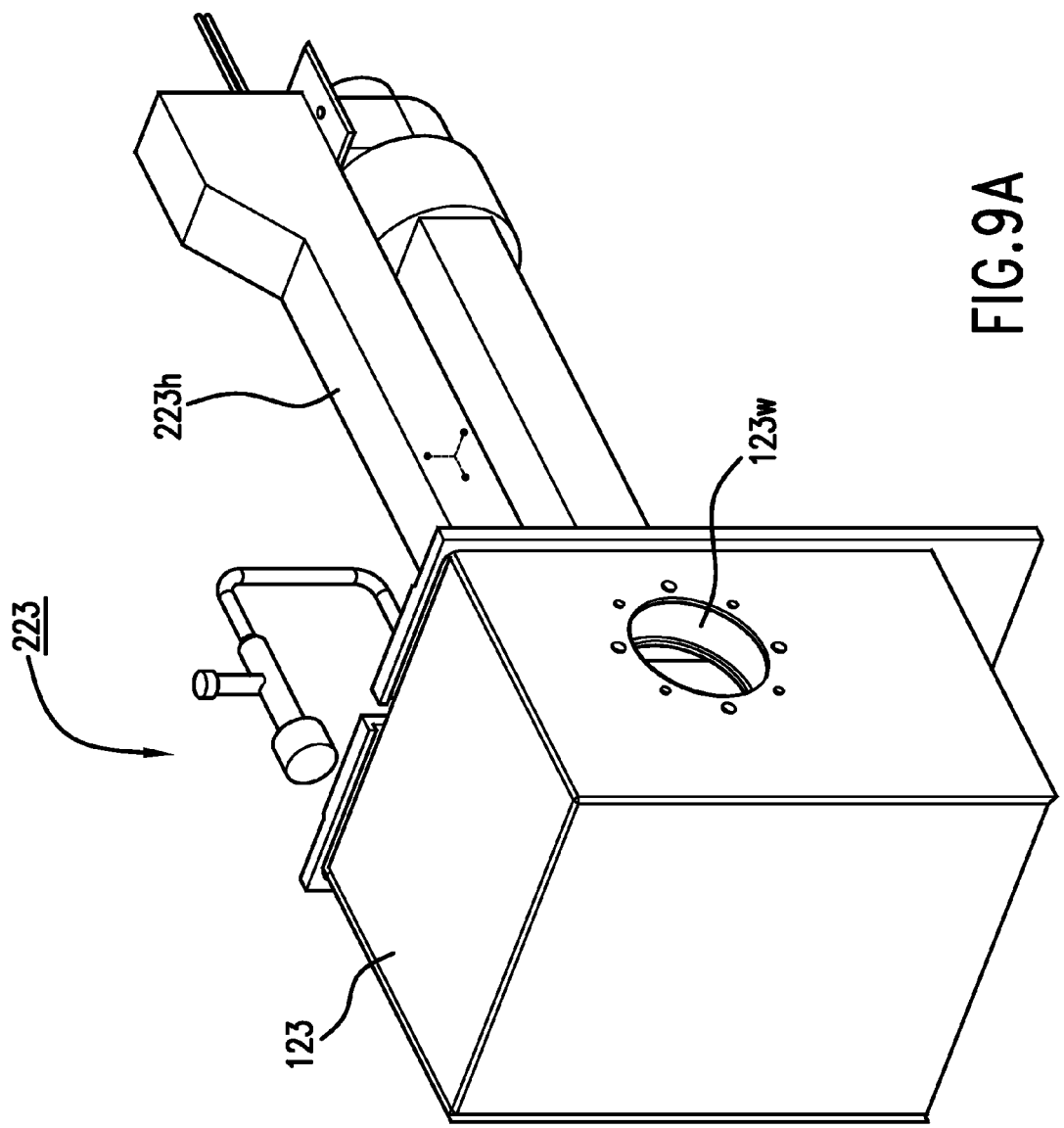

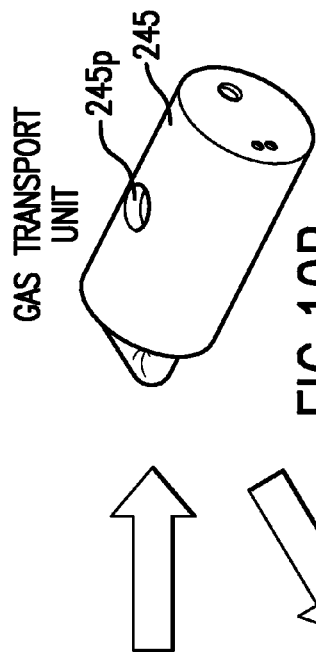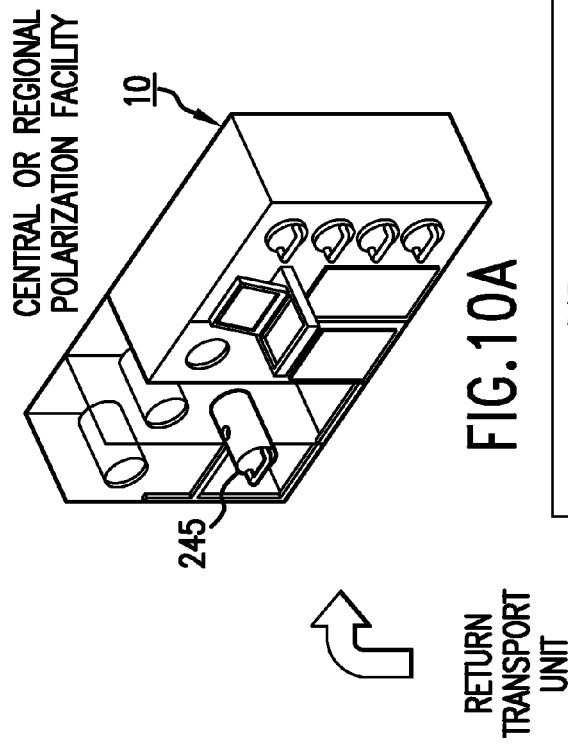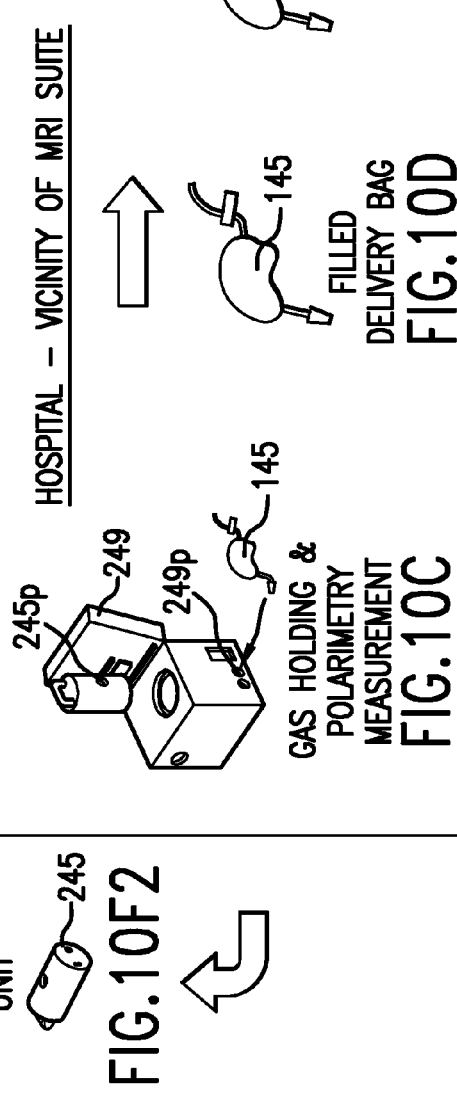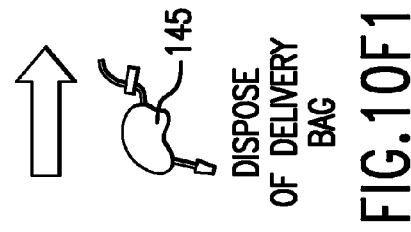

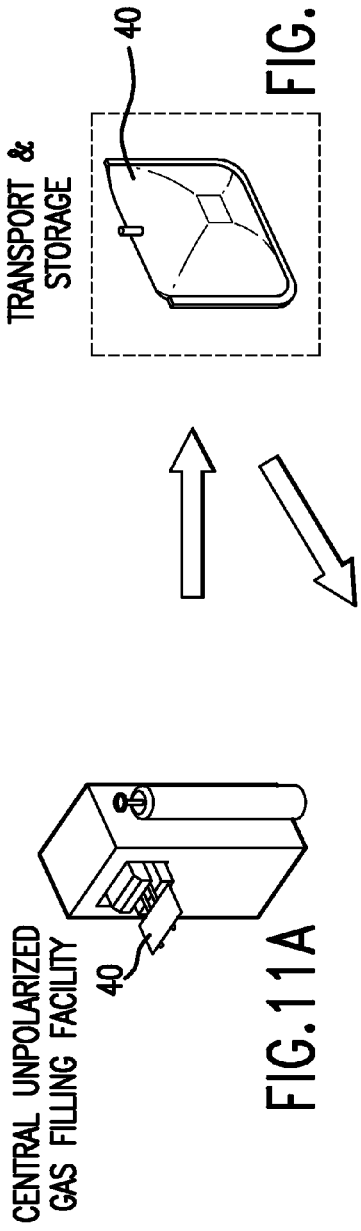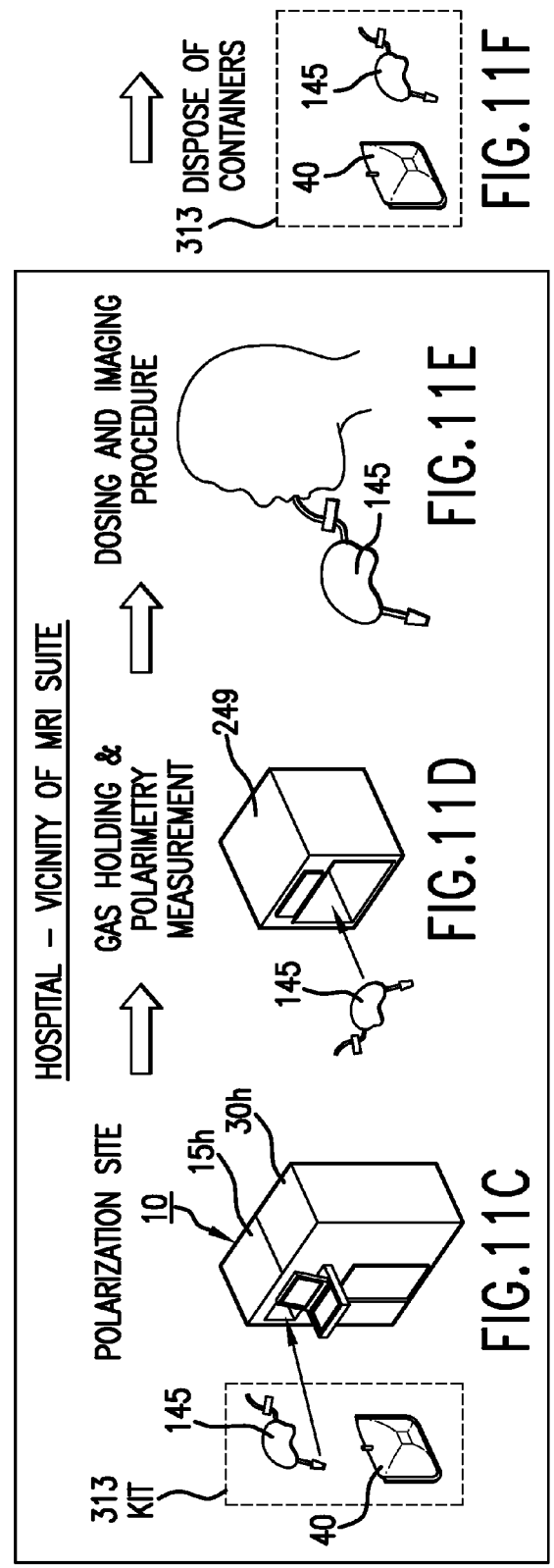

OPTICAL PUMPING MODULES, POLARIZED GAS BLENDING AND DISPENSING SYSTEMS, AND AUTOMATED POLARIZED GAS DISTRIBUTION SYSTEMS AND RELATED DEVICES AND METHODS

This application is a divisional of U.S. application Ser. No. 10/277,909 filed Oct. 22, 2002 now U.S. Pat. No. 7,287,390, which claims priority to U.S. application No. 60/335,706 filed Oct. 22, 2001, the entire disclosure of which is hereby incorporated by reference.

FIELD OF THE INVENTION

The present invention relates to the production of polarized noble gases used in NMR and magnetic resonance imaging ("MRI") applications.

BACKGROUND OF THE INVENTION

It has been discovered that polarized inert noble gases can produce improved MRI images of certain areas and regions of the body that have heretofore produced less than satisfactory images in this modality. Polarized helium-3 ("$^3$He") and xenon-129 ("$^{129}$Xe") have been found to be particularly suited for this purpose. Unfortunately, as will be discussed further below, the polarized state of the gases is sensitive to handling and environmental conditions and can, undesirably, decay from the polarized state relatively quickly.

Hyperpolarizers are used to produce and accumulate polarized noble gases. Hyperpolarizes artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images of the substance in the body. See U.S. Pat. Nos. 5,545,396; 5,642,625; 5,809,801; 6,079,213, and 6,295,834; the disclosures of these patents are hereby incorporated by reference herein as if recited in full herein.

In order to produce the hyperpolarized gas, the noble gas is typically blended with optically pumped alkali metal vapors such as rubidium ("Rb"). These optically pumped metal vapors collide with the nuclei of the noble gas and hyperpolarize the noble gas through a phenomenon known as "spin-exchange." The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange."

Generally stated, as noted above, conventional hyperpolarizers include an optical pumping chamber held in an oven and in communication with a laser source that is configured and oriented to transmit circularly polarized light into the optical pumping chamber during operation. The hyperpolarizers may also monitor the polarization level achieved at the polarization transfer process point, i.e., at the optical cell or optical pumping chamber. In order to do so, typically a small "surface" NMR coil is positioned adjacent the optical pumping chamber to excite and detect the gas therein and thus monitor the level of polarization of the gas during the polarization-transfer process. See U.S. Pat. No. 6,295,834 for further description of polarization monitoring systems for optical pumping cells and polarizers.

In any event, it is now known that on-board hyperpolarizer monitoring equipment no longer requires high-field NMR equipment, but instead can use low-field detection techniques to perform polarization monitoring for the optical cell at much lower field strengths (e.g., 1-100 G) than conventional high-field NMR techniques. This lower field strength allows correspondingly lower detection equipment operating frequencies, such as 1-400 kHz. More recently, Saam et al. has proposed a low-frequency NMR circuit expressly for the on-board detection of polarization levels for hyperpolarized $^3$He at the optical chamber or cell inside the temperature-regulated oven that encloses the cell. See Saam et al., *Low Frequency NMR Polarimeter for Hyperpolarized Gases*, Jnl. of Magnetic Resonance 134, 67-71 (1998). Others have used low-field NMR apparatus for on-board polarization measurement.

After the spin-exchange has been completed, the hyperpolarized gas is typically separated from the alkali metal prior to introduction into a patient (to form a non-toxic pharmaceutically acceptable product). Unfortunately, both during and after collection, the hyperpolarized gas can deteriorate or decay relatively quickly (lose its hyperpolarized state) and therefore must be handled, collected, transported, and stored carefully. Thus, handling of the hyperpolarized gases is critical, because of the sensitivity of the hyperpolarized state to environmental and handling factors and the potential for undesirable decay of the gas from its hyperpolarized state.

As demand for the polarized gas increases, there is a need for methods and systems that can provide increased volume production of the polarized gas to meet production demands in a manner that provides a reliable supply of polarized gas in a relatively economic manner that can consider and facilitate hospital or clinical scheduling of associated equipment (MRI or NMR systems).

OBJECTS AND SUMMARY OF THE INVENTION

In view of the foregoing, it is an object of the present invention to provide hyperpolarizers, systems, methods, and computer program products to produce, blend, and/or dispense polarized gases.

It is an additional object of the present invention to provide an automated hyperpolarizer that can produce polarized gases.

It is another object of the present invention to provide a hyperpolarizer that can be operated at the point-of-use.

Other objects of the present invention are to providing improved thermal systems for optical pumping cells, measured gas blending systems, and/or automated polarized noble gas handling systems.

Another object of the present invention is a fluid distribution manifold for automated polarized noble gas handling systems.

These and other objects are satisfied by the present invention by integrated-gas distribution systems with gas blending, and/or gas dispensing systems.

Certain embodiments of the present invention are directed to hyperpolarizers for producing polarized noble gases. The hyperpolarizers include a control module configured to direct the operation of the hyperpolarizer to produce polarized noble gas via spin-exchange interactions between a noble gas and an alkali metal and at least one optical pumping module including an optical pumping cell operably associated with the control module. The hyperpolarizer also includes a dispensing system operably associated with the control module and the optical pumping module to dispense meted volumes of polarized gas from the hyperpolarizer and a fluid distribution system operably associated with the control module, the optical pumping module, and the dispensing system. In response to commands transmitted from the control module, the fluid distribution system operates to: (a) automatically direct purge gas into and out of a gas travel path that extends from the control module to the optical pumping cell prior to commencing the spin-exchange interactions in the optical pumping cell, (b) then receives unpolarized gas and directs it to travel in the gas travel path to the optical pumping cell, and (c) post-polarization, automatically directs polarized gas from the optical pumping cell into a polarized gas exit travel path to the dispensing system.

Other embodiments are directed to methods of providing polarized noble gas for NMR or MRI applications. The method includes: (a) expelling an unpolarized gas mixture comprising a noble gas to be polarized from a pre-packaged container into a hyperpolarizer having an unpolarized gas receiving port, an optical pumping cell, and a polarized gas dispensing port; (b) polarizing the noble gas via spin-exchange interactions with an alkali metal in the hyperpolarizer; (c) automatically blending in situ the polarized noble gas with a biocompatible fluid to provide a pharmaceutical grade polarized noble gas product suitable for in vivo administration to a subject; and (d) dispensing the polarized noble gas product into a patient delivery container.

In particular embodiments, the method can include directing the polarized gas into a syringe having a plunger that is configured to controllably automatically translate to control the volume of polarized gas received in the syringe to provide a measured amount of polarized gas before the dispensing step.

Other embodiments of the present invention are directed to hyperpolarizers that include: a controller; a purge gas source; a vacuum pump; an optical pumping cell having a gas inlet port and a gas outlet port; a laser operably associated with the optical pumping cell; an oven encasing the optical pumping cell; and a block manifold in fluid communication with the optical pumping cell, the purge source, and the vacuum pump, the manifold having internally extending selectable alternative gas flow paths therein, the gas flow paths including a purge gas flow path, and a polarized gas flow path with a polarized gas exit port, wherein the manifold comprises a plurality of individually automatically operable valves that open and close selectively in response to a command signal from the controller to allow the noble gas to be delivered to the optical cell and polarized and then to travel through the polarized gas exit port.

An additional embodiment of the present invention is an optical pumping cell thermal assembly. The assembly includes: an optical pumping cell and an oven with a laser window formed therein encasing the optical pumping cell. The assembly also includes an elongated housing extending from the oven an axial distance away therefrom. The housing has a cool air venturi formed therein. The assembly also includes a heating element disposed in the elongated housing and a fan disposed in the housing at an end portion away from the oven in fluid communication with the heating element and the cool air venturi. In operation, the oven is configured to have a temperature of between about 150-200° C., and wherein the optical pumping thermal assembly is configured to have a substantially closed thermal system to reduce the power requirement or on time of the heating element.

Another embodiment is directed to a computer program product for operating a hyperpolarizer having at least one optical pumping cell to produce polarized noble gas and a fluid distribution and dispensing system with remote-actuated valves that open and close to direct the flow of gas therein. The computer program product includes a computer readable storage medium having computer readable program code embodied in said medium, said computer-readable program code comprising: computer readable program code that automatically transmits control signals to the remote actuated valves during operation of the hyperpolarizer to cause selected valves to open and/or close at appropriate times so as to: (a) cause purge gas to travel through the fluid distribution system and into the optical pumping cell; (b) evacuate the purge gas from the optical pumping cell and the fluid distribution system; (c) direct an unpolarized gas mixture into the fluid distribution system and into the optical pumping cell for spin-exchange polarization; and then (d) direct polarized gas to exit the optical pumping cell and travel in the fluid distribution system to the dispensing system.

Advantageously, the present invention can provide improved hyperpolarizers. Certain embodiments provide systems and devices that can handle polarized gas in an automated or semi-automated manner and that can produce patient-sized pharmaceutical grade quantities (such as 0.5-2 liters) of polarized gas in a manner that can reduce the labor involved therewith can be produced to support to the clinic or hospital.

The foregoing and other objects and aspects of the present invention are explained in detail herein.

BRIEF DESCRIPTION OF THE DRAWINGS

FIG. 8B is a front perspective view of an example manifold assembly with valves corresponding to the system shown in FIG. 6B according to embodiments of the present invention.

FIG. 8C is a rear perspective view of the device in FIG. 8B.

FIG. 8D is a side view of the device shown in FIG. 8B.

FIG. 8E is a different side view of the device shown in FIG. 8B.

FIG. 8F is front perspective view of a nitrogen manifold assembly corresponding to the system shown in FIG. 6B according to embodiments of the present invention.

FIG. 8G is a rear perspective view of the device shown in FIG. 8F.

FIG. 8H is a top view of the device shown in FIG. 8F.

FIG. 8I is a side view of the device shown in FIG. 8F.

FIG. 9A is a side perspective view of an optical module thermal system according to embodiments of the present invention.

FIG. 10 is a schematic illustration of a central or regional polarized gas distribution model according to embodiments of the present invention. FIGS. 10A-10E illustrate steps associated therewith and FIGS. 10F1 and 10F2 illustrate post-use steps according to embodiments of the present invention.

FIG. 11 is a schematic illustration of point of use (hospital or clinical facility or portable system positioned) with the hyperpolarizer positioned proximate an MRI suite. FIGS. 11A-11E illustrate steps associated therewith while FIG. 11F illustrates a post-processing step.

DETAILED DESCRIPTION OF EMBODIMENTS OF THE INVENTION

Figure 1A:
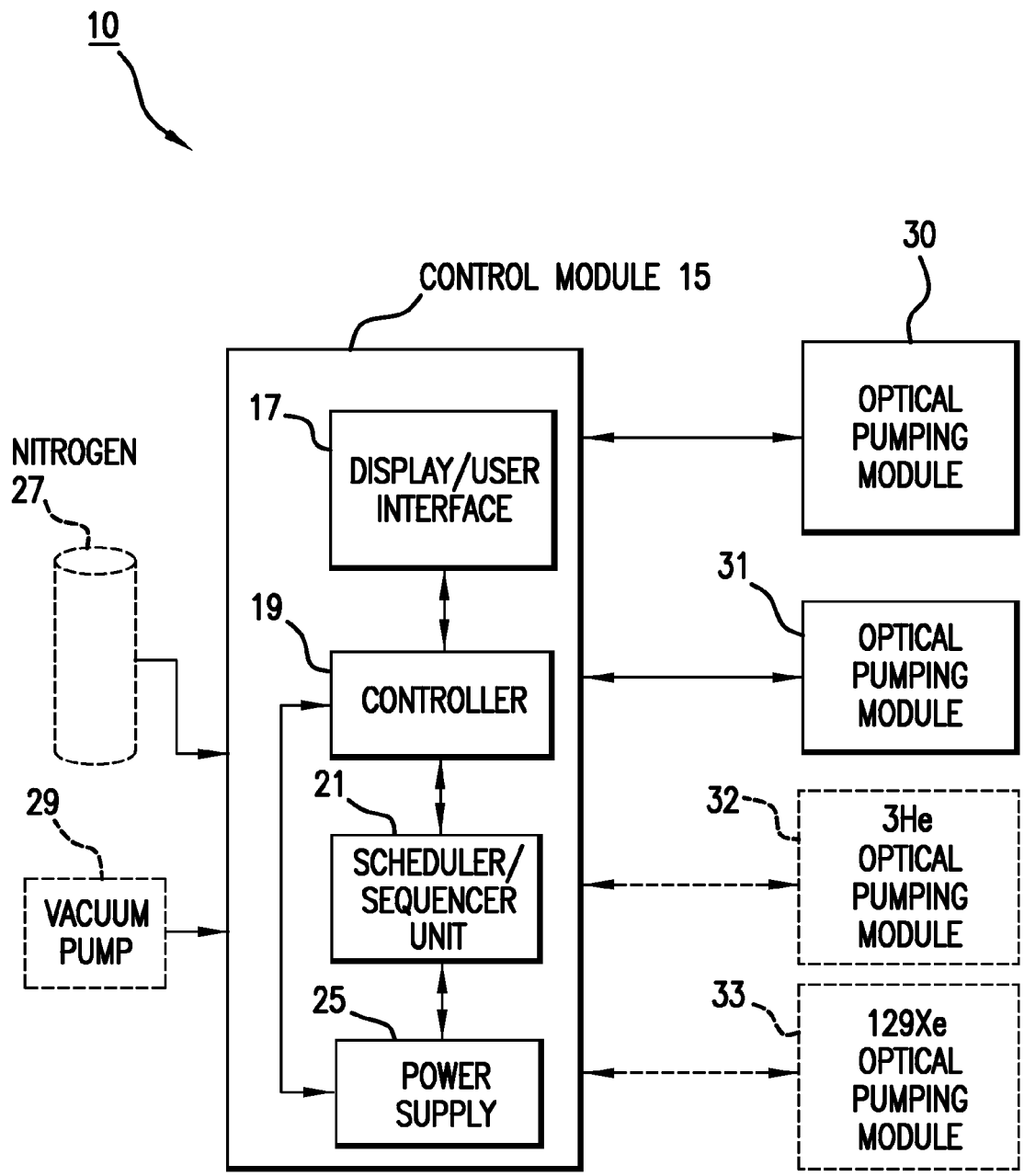
FIG. 1A is a block diagram of a hyperpolarizer with a control module and a plurality of optical pumping modules according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the drawings, layers, regions, or components may be exaggerated for clarity. In the figures, broken lines in the flow charts indicate optional features.

In the description of the present invention that follows, certain terms may be employed to refer to the positional relationship of certain structures relative to other structures. As used herein the term "forward" and derivatives thereof refer to the general direction the gas mixture travels as it moves through the hyperpolarizer unit; this term is meant to be synonymous with the term "downstream," which is often used in manufacturing environments to indicate that certain material being acted upon is farther along in the manufacturing process than other material. Conversely, the terms "rearward" and "upstream" and derivatives thereof refer to the directions opposite, respectively, the forward and downstream directions.

Also, as described herein, polarized gases are collected and may, in particular embodiments, be frozen, thawed, and then used in MRI or NMR spectroscopy applications. For ease of description, the term "frozen polarized gas" means that the polarized gas has been frozen into a solid state. The term "liquid polarized gas" means that the polarized gas has been or is being liquefied into a liquid state. Thus, although each term includes the word "gas," this word is used to name and descriptively track the gas that is produced via a hyperpolarizer to obtain a polarized "gas" product. Thus, as used herein, the term "gas" has been used in certain places to descriptively indicate a hyperpolarized noble gas product and may be used with modifiers such as solid, frozen, and liquid to describe the state or phase of that product. The polarized gas product may include other constituents such as other carrier gases or carrier liquids as desired.

Various techniques have been employed to accumulate and capture polarized gases. For example, U.S. Pat. No. 5,642,625 to Cates et al. describes a high volume hyperpolarizer for spin-exchange polarized noble gas and U.S. Pat. No. 5,809,801 to Cates et al. describes a cryogenic accumulator for spin-polarized $^{129}$Xe. As used herein, the terms "hyperpolarize," "polarize," and the like, are used interchangeably and mean to artificially enhance the polarization of certain noble gas nuclei over the natural or equilibrium levels. Such an increase is desirable because it allows stronger imaging signals corresponding to better MRI images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396.

The present invention is described in certain portions of the specification with reference to flowchart illustrations and/or block diagrams of methods, and computer program products according to certain embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, embedded processor or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

As will be appreciated by one of skill in the art, the present invention may be embodied as a method, data or signal processing system, computer program product, and may include certain electro-mechanical or hardware components. Accordingly, certain embodiments of the present invention may take the form of an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java☐, Smalltalk or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain of the flowcharts and block diagrams illustrate methods to operate hyperpolarizers or components thereof to yield polarized gas according to embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Referring to FIG. 1A, this block diagram illustrates one embodiment of a modular hyperpolarizer 10. As shown, the primary modules include a control module 15 and a plurality of optical pumping modules 30, 31 with two more optical pumping modules 32, 33 optionally available. The plurality of optical pumping modules can be provided in any suitable quantity such as two, three, four or more. As such, the hyperpolarizer 10 can be configured to operate with one or more optical pumping modules and still have the capacity to add additional modules as production demands increase. Alternatively, the hyperpolarizer 10 can be manufactured with all available optical pumping module spaces filled. This modular configuration and operation can allow for site customization (to meet a particular production site's capacity requirements). In addition, field repairs may be improved by using modular replacement parts.

Figure 1B:
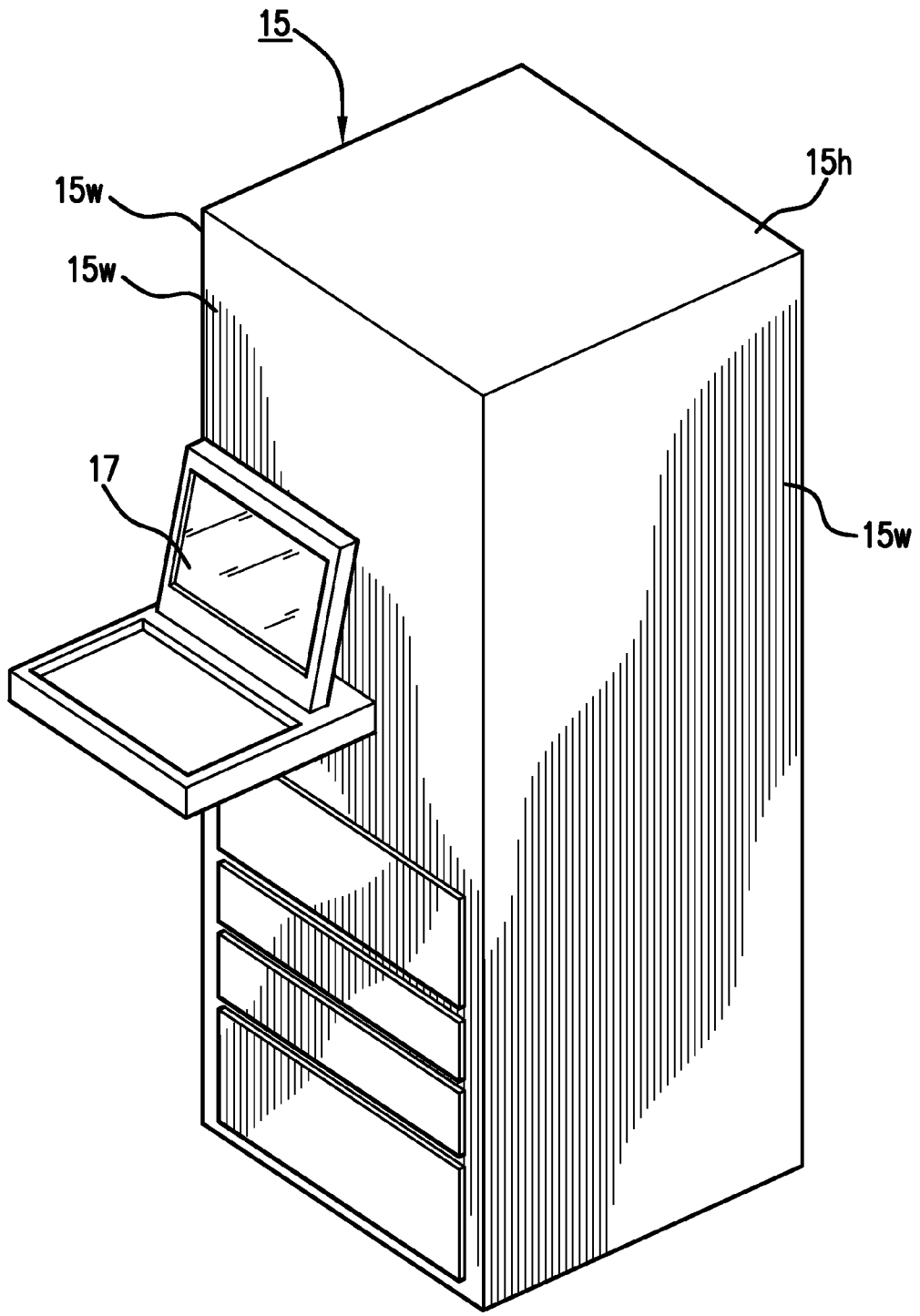
FIG. 1B is a perspective view of a control module for a hyperpolarizer according to embodiments of the present invention.

The hyperpolarizer 10 also includes a source of high purity purge gas 27 (such as grade 5 Nitrogen) and a vacuum pump 29. As shown, the purge gas 27 and vacuum pump 29 are configured to engage with the control module 15. As shown in FIG. 1B, the control module 15 can be held in a housing 15$h$ with upstanding sidewalls 15$w$. At least one of the sidewalls 15$w$ can be configured to provide access to the operational mating (electrical and mechanical) components 15$c$ (FIG. 1C) between the optical pumping modules and the control module to allow fluid or electrical control attachments for one or more of: air (compressed) or hydraulic fluid for automated controls; and fluid for exchange via the gas/purge plumbing; and electrical connections. The control module housing 15$h$ can be configured to have a reduced footprint to reduce the space demand to support the equipment in the production environment or facility.

As shown in FIG. 1A, the control module 15 also includes a display/user interface 17, a controller 19 that controls the operation of the hyperpolarizer 10, a scheduler/sequencer unit 21, and a power supply 25.

The display and/or user interface or input means 17 can include a monitor as well as a keyboard or touch screen or the like that can allow an operator to input patient scheduling information to allow the hyperpolarizer 10 to determine or forecast a desired production operation schedule to meet the patient use demands. In other embodiments, the user interface can be configured to allow remote input of the scheduling via a computer network, whether, local, regional, national (intranet) or global (internet). The display or interface 17 can also display or relay information regarding the operational status and function of the hyperpolarizer 10 such as the polarization level of the gas in the optical pumping module(s) 30, 31 or any detected operational errors or discrepancies during operation.

Figure 1C:
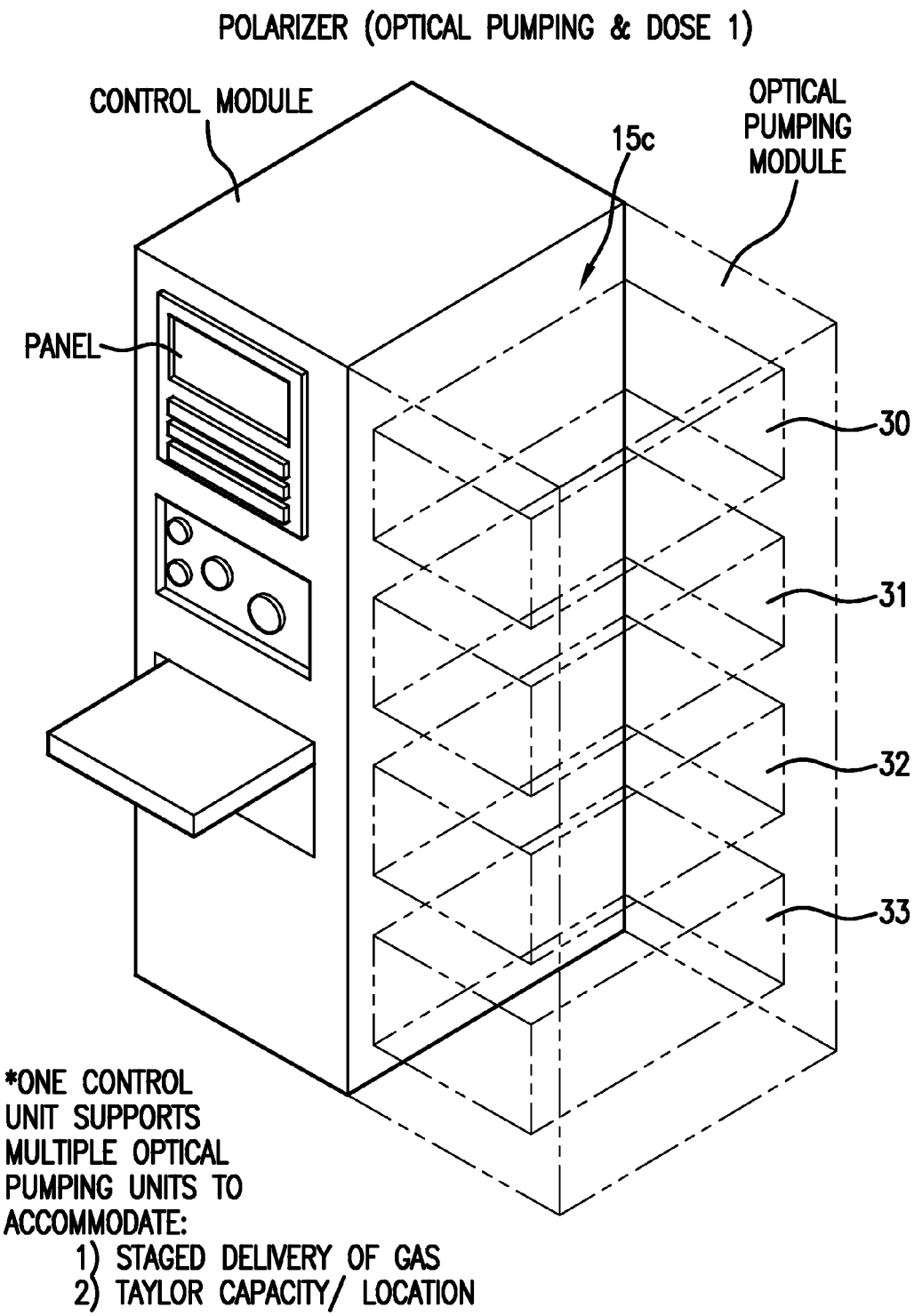
FIG. 1C is a perspective view of a hyperpolarizer with a control module and a plurality of optical pumping modules according to embodiments of the present invention.

As also shown in FIG. 1A, the optical pumping modules may be either as all $^3$He modules, all $^{129}$Xe modules, or a combination of desired numbers of both $^3$He and $^{129}$Xe modules (such as two $^3$He, and one $^{129}$Xe). FIG. 1C illustrates that the hyperpolarizer 10 can include side-by-side matable housings: one for the control module 15$h$, and one for the optical pumping modules 30$h$. The optical pumping modules 30, 31 (that may include additional modules 32, 33) can be arranged to be vertically stacked in alignment. This arrangement can reduce the space requirement for the equipment at the production facility. The optical pumping modules 30, 31 may be configured to slide into cavities or shelves formed in the housing 30$h$ (not shown) (so as to position the modules to be spaced apart a distance), or may be configured as self-stacking units or pairs of units so that two or more of the modules 30, 31, (and/or 32, 33) contact each other when in position.

As will be understood by those of skill in the art, in certain embodiments, the control module 15 is configured to provide the purge/pump capacity from a central purge gas source 27 and vacuum pump 29 to each of the optical pumping modules 30, 31. As such, fluid flow paths of plumbing extending between the purge and vacuum sources to each of the optical pumping modules are defined by a fluid distribution system or manifold network of plumbing, valves, and solenoids. These fluid flow paths selectively direct purge gas to and from the optical pumping cells 30, 31 to purge and evacuate the optical pumping modules and related flow paths in order to prepare them for polarization operation.

Figure 2:
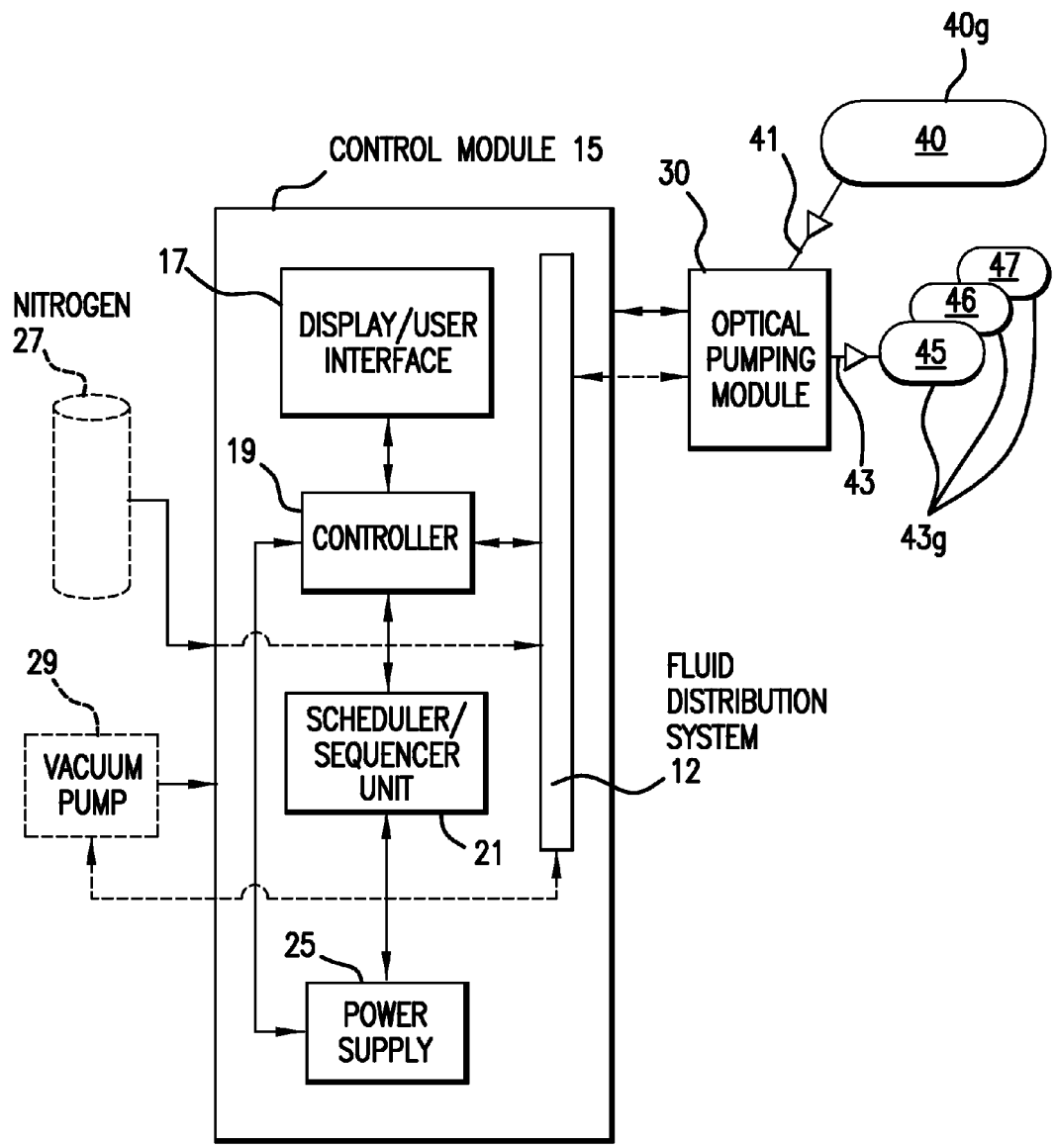
FIG. 2 is a block diagram of a control module and an optical pumping module according to embodiments of the present invention.

FIG. 2 illustrates the control module 15 with a fluid distribution system 12 that is in fluid communication with the purge gas source 27 and the vacuum pump 29 (shown by the broken line between these components and the fluid distribution system 12) and that is operably associated with the controller 19. The fluid distribution system 12 is also in fluid communication with the optical pumping module 30 (and the other modules that may be attached to or connected with the control module 15), as is also indicated by the broken line therebetween in the figure.

Generally stated, the scheduler/sequencer unit 21 determines the appropriate operational sequence and production run schedule(s) of one or more of the optical pumping cells to meet user requirements (recognizing that there is a limited life to the polarized gas and, hence a limited shelf life). The controller 19 initiates the pump/purge preparation process proximate in time to the desired production operation schedule to clean and prepare the optical pumping cell and associated plumbing for receiving an unpolarized quantity of noble gas mixture and to begin the spin-exchange polarization process each time an optical module is scheduled for a production run.

As shown in FIG. 2, a quantity of pre-packaged unpolarized gas mixture in a container 40 is received at a gas access (inlet) port 41 on the optical pumping module 30. The quantity can be sized so as to provide the constituents commensurate with that needed to form a single batch. Typically, the pre-packaged unpolarized gas mixture comprises a minor amount of the target noble gas and a larger quantity of one or more high purity biocompatible filler gases. For example, for $^3$He polarization, an unpolarized gas blend of $^3$He/$N_2$ can be about 99.25/0.75. For producing hyperpolarized $^{129}$Xe, the pre-mixed unpolarized gas mixture can be about 85-98% He (preferably about 85-89% He), about 5% or less $^{129}$Xe, and about 1-10% $N_2$ (preferably about 6-10%).

The pre-packaged amount of unpolarized gas mixture in the container (and the optical cell itself) can be meted out and configured and sized so that the single batch production run quantity provides a single patient amount for a single MRI imaging or NMR evaluation session. To provide the pharmaceutical grade polarized gas doses, the polarized gas itself may be mixed with pharmaceutical grade carrier gases or liquids, or may be configured to be administered as the only or primary substance or constituent. In particular embodiments, the polarized gas is $^3$He and is mixed with nitrogen filler gas to form a volume of gas blend to be inhaled by the patient. In other embodiments, for example, for producing inhalable $^{129}$Xe, the $^{129}$Xe may form a major portion (or all) of the administered dose. In other embodiments, the polarized gas can be formulated to be injected in vivo (in a liquid carrier, in microbubble solution, or in gaseous form).

In any event, as illustrated in FIG. 2 by the plurality of receiving containers 45, 46, 47, attached to a polarized gas exit port 43 of the optical pumping module 30, the volume of polarized gas produced per batch can be sufficient to provide polarized gas or polarized gas blend in sufficient amounts to yield a plurality of separate (inhalable) boluses administered to the subject over a single NMR or MRI session.

Although shown as separate features, the polarized gas exit port 43 may be the same port as the inlet port 41.

Figure 3A:
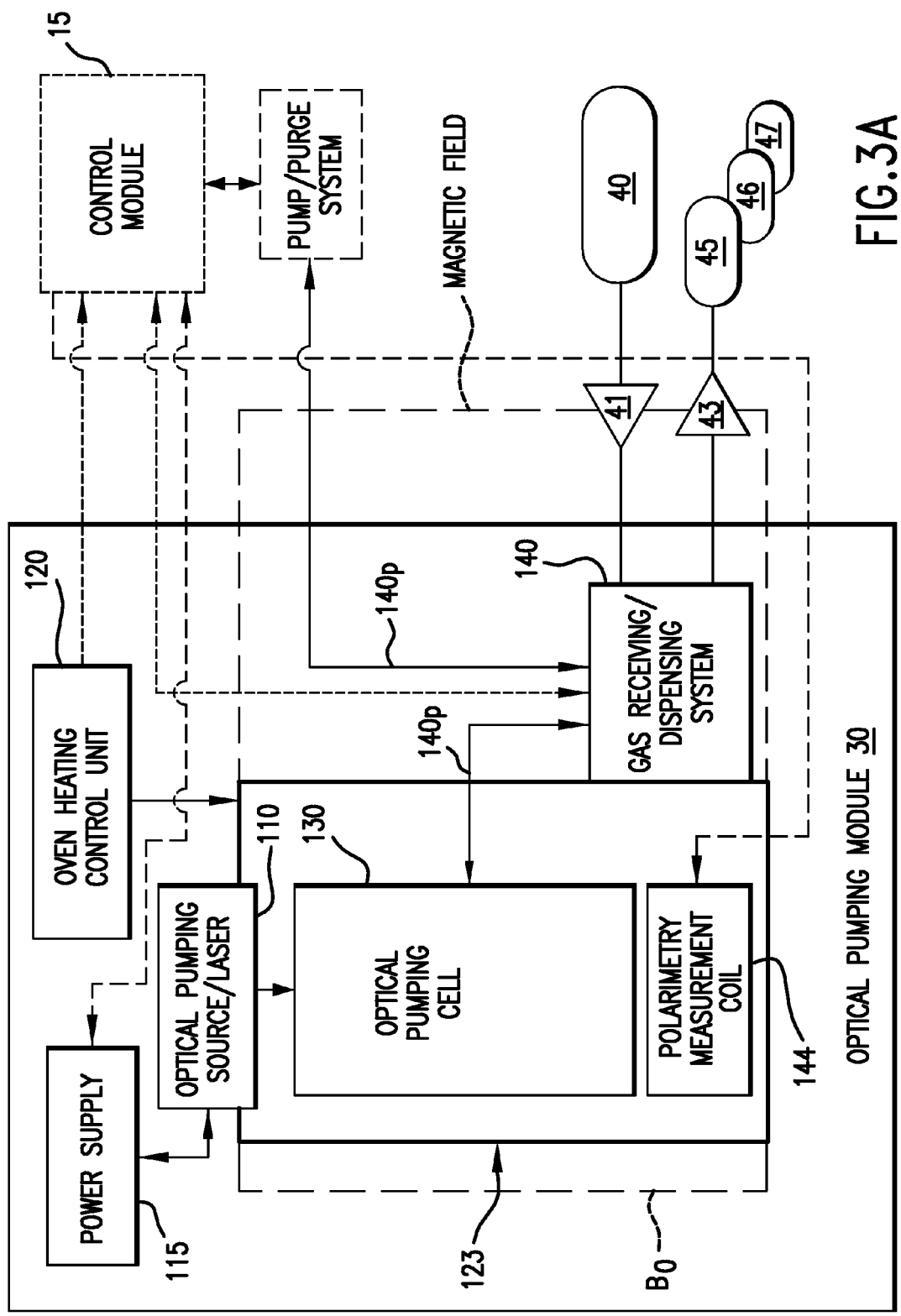
FIG. 3A is a block diagram of an optical pumping module according to embodiments of the present invention.

FIG. 3A illustrates one embodiment of an optical pumping module 30. As shown, the optical pumping module 30 includes a power supply 115, an optical pumping cell 130, an oven 123 configured to encase the optical pumping cell 130, an oven heating control unit 120 (that can include heat sensors and the like, which are not shown), an optical pumping source 110 (such as a laser, and in particular embodiments a diode laser array), a polarimetry measurement coil 144, a gas receiving/dispensing system 140, and plumbing 140p (with valves and solenoids or actuators) defining the selectable fluid flow paths for purge gas and polarized gas. The optical module 30 can also include a magnetic field source capable of generating a magnetic field $B_0$ (shown by the dark broken lines that cover a portion of the optical pumping module and extends to cover the gas dispensing port 43). The field $B_0$ may be further generated, formed or shaped to extend to cover the receiving containers of polarized gas 45, 46, 47 during dispensing. The field source may be a pair of Helmholtz coils as is well known to those of skill in the art. In other embodiments, the field source can be a solenoid. The solenoid can be configured to surround the optical pumping cell. The polarized gas can be dispensed from the optical pumping module by directing the gas to flow or dispense along the axis of the solenoid. Suitable solenoid field sources and configurations are described in co-assigned, co-pending U.S. patent application Ser. No. 09/333,571, the contents of which are hereby incorporated by reference as if recited in full herein.

In other embodiments, the optical modules housing 30h itself can include or be configured to generate one or more magnetic fields for the optical pumping modules (not shown).

In operation, for each production run on each pumping module, after the control module 15 has directed the evacuation and gas-purging of the optical pumping cell 130 and related plumbing 140p, the pre-packaged container 40 holding the unpolarized gas mixture 40g is opened and the gas directed into the optical pumping module 30 and into the optical pumping cell 130. The container 40 may be a collapsible bag sized so that the pre-packaged amount of unpolarized gas does not completely fill the capacity and, instead, only partially fills the volumetric capacity thereof. For example, filling to about 30-60% capacity may provide a suitable expansion factor. This can allow for expansion of the gas during transport at increased altitudes or other environmental or shipping conditions.

The hyperpolarizer 10 can include one or more purifiers or filters (27f, 41f, FIG. 6A) can be positioned in line with the plumbing to remove impurities such as water vapor, alkali metal (post polarization), and oxygen from the system (or to inhibit their entry therein). The hyperpolarizer 10 can also include various sensors including a flow meter as well as a plurality of valves as well as electrical solenoids, and/or hydraulic or pneumatic actuators that can be controlled by the controller 19 to define the fluid flow path and operation of the components of the hyperpolarizer 10. As will be understood by those of skill in the art, other flow control mechanisms, and devices (analog and electronic) may be used as contemplated by the present invention.

Again referring to FIG. 3A, generally stated, the optical pumping source 110 is a light source such as a laser (i.e., a diode laser array) directed into the optical pumping (or polarizer) cell 130 through various focusing and light distributing means, such as lenses, mirrors, and the like (not shown). In certain embodiments, the laser is circularly polarized to optically pump alkali metal held in the cell 130. The cell 130 is positioned inside a temperature-regulated oven 123 (illustrated by a heavy line). The temperature during polarization may be between 170-200° C.

Generally described, the optical pumping modules 30, 31 are configured to polarize noble gas via spin-exchange. The unpolarized pre-packaged gas mixture is introduced into the polarizer optical pumping cell 130. The polarization process can be relatively lengthy, depending on the type of gas and amount of polarized gas desired. For example, a typical $^3$He polarization time of typical single patient dose amounts can be from about 1 hour-6 hours, while $^{129}$Xe may be configured to produce a single patient dose of about 1 liter in about 1-3 hours and typically in under about 60-90 minutes.

For $^{129}$Xe "continuous" flow based polarization, the typical residence time of the gas in the cell 130 is about 10-30 seconds; i.e., it takes on the order of 10-30 seconds for the gas mixture to be hyperpolarized while moving through the cell 130. The polarizer cell 130 can be a high-pressure optical pumping cell. During operation, the oven 123 defines a heated chamber with apertures configured to allow entry of the laser-emitted light into the optical pumping cell 130. A vaporized alkali metal such as Rb is introduced into the polarizer cell 130. The Rb vapor is optically pumped via the optic light source.

The optical cell can also employ helium as a buffer-gas to pressure broaden the Rb vapor absorption bandwidth. The selection of a buffer gas is important because the buffer gas—while broadening the absorption bandwidth—can also undesirably impact the alkali metal-noble gas spin-exchange by potentially introducing an angular momentum loss of the alkali metal to the buffer gas rather than to the noble gas as desired.

As will be appreciated by those of skill in the art, Rb is reactive with $H_2O$. Therefore, any water or water vapor introduced into the polarizer cell 130 can cause the Rb to lose laser absorption and decrease the amount or efficiency of the spin-exchange in the polarizer cell 130. Thus, as an additional precaution, an extra filter or purifier can be positioned before the inlet of the polarizer cell 130 with extra surface area to remove even additional amounts of this undesirable impurity in order to further increase the efficiency of the hyperpolarizer 10.

In any event, once the polarization process is complete, polarized gas exits the optical pumping cell 130, and is ultimately directed to gas dispensing system 140 and then to a collection or accumulation container such as a patient delivery container or drug container (see FIGS. 3A and 45-47 and FIG. 5D).

Figure 3B:
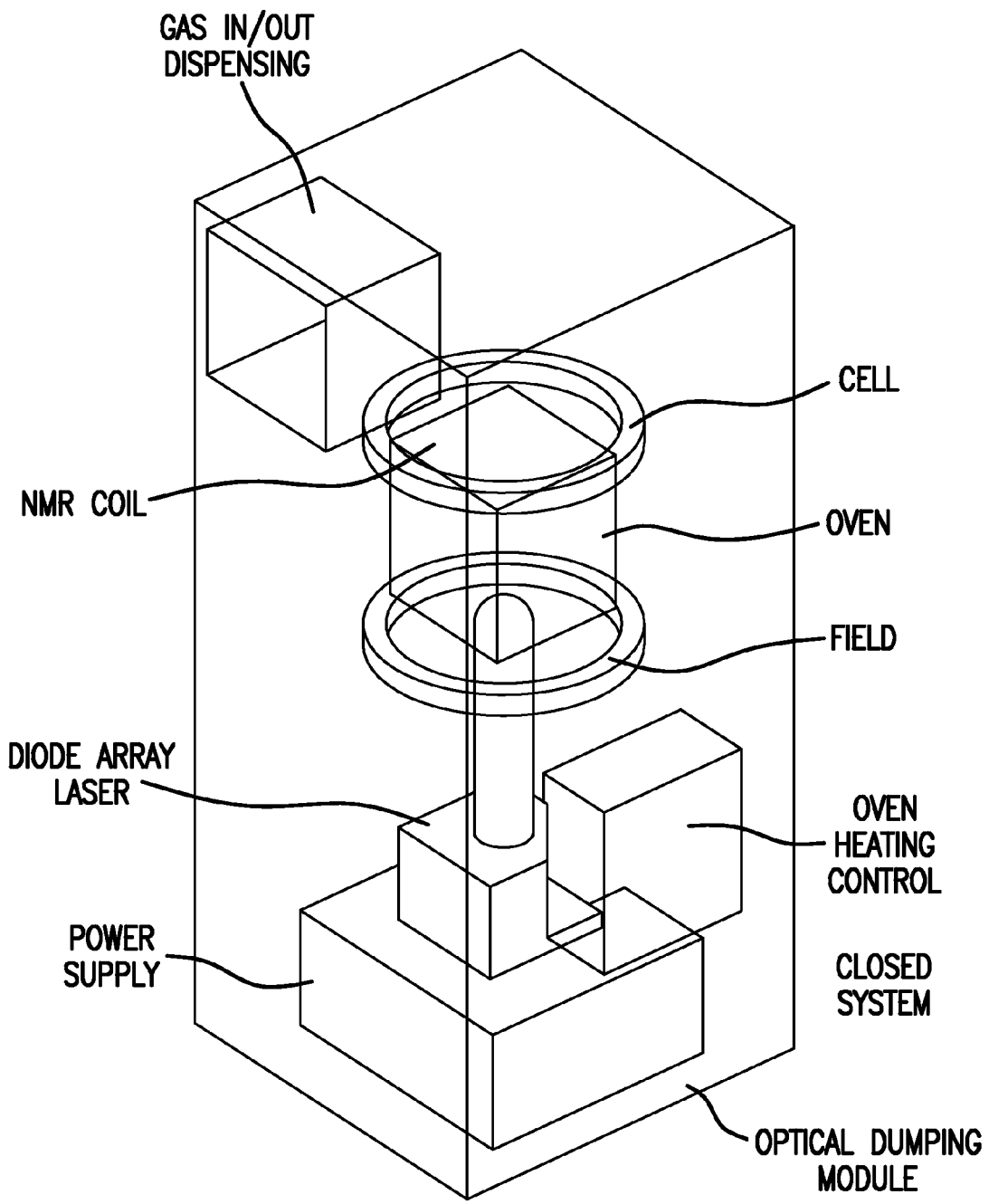
FIG. 3B is a perspective view of a modular optical pumping cell according to embodiments of the present invention.

FIG. 3B illustrates one embodiment of a modular self-contained optical pumping module 30. As shown, certain components are arranged so that they are axially aligned. As shown, the components are serially identified as: the power supply 115; the oven heating control unit 120; the oven 123 and the optical pumping cell 130 therein with the gas in/out dispensing module 140 located so that it is externally accessible. Other portions of the manifold (i.e., the flow path defined by plumbing, valves, and the like), are not shown for ease of illustration). Thus, the laser 110 axially extends such that it is proximate to the oven 123 that holds the optical pumping cell 130 therein. The Helmholtz coil pair $132_1$, $132_2$ are arranged on opposing sides of the oven and optical cell, 123, 130, respectively. In other embodiments, a cylindrical solenoid can be configured to surround the optical cell (not shown).

The hyperpolarizer unit 10 can also include a cooling means to cool the optical pumping cell 130 after the polarization process. The cooling means can include a refrigeration source that can turn the oven 123 into a cooling chamber or that can be located along the plumbing or exit flow path (such as in the gas dispensing line) to precipitate the alkali metal from the polarized gas stream. In other embodiments, heat to the oven 123 is turned off and natural cooling is used to condense the Rb out of the vapor phase and collect it in the bottom of the optical pumping cell 130. In addition, a micropore filter can be positioned in the gas dispensing line or in the exit flow path (extending between the optical cell exit port to the dispensing port). As will be appreciated by one of skill in the art, the alkali metal can precipitate out of the gas stream at temperatures of about 40° C. Other filtering means can also be used, such as, but not limited to, an alkali metal reflux condenser (not shown). The refluxing condenser employs a vertical refluxing outlet pipe that can be kept at room temperature. The gas flow velocity through the refluxing pipe and the size of the refluxing outlet pipe is such that the alkali metal vapor condenses and drips back into the pumping cell by gravitational force. In any event, it is desirable to remove alkali metal prior to delivering polarized gas to a patient to provide a non-toxic, sterile, or pharmaceutically acceptable substance (i.e., one that is suitable for in vivo administration).

Typically, the polarized $^{129}$Xe is then accumulated in a cold finger where it is frozen and subsequently thawed to provide the polarized $^{129}$Xe in the dose mixture. Additional description of suitable polarizers and cold fingers is included in U.S. Pat. Nos. 5,642,625, 5,809,801, and 6,709,213, the contents of which are hereby incorporated by reference as if recited in full herein.

A delivery or receiving container such as a patient dose bag or other vessel can be attached to the dispensing outlet 43 (FIG. 2). A valve or other device located on the device can be opened to evacuate the attached bag. Once the bag is evacuated, the polarized gas can be directed into the bag directly or into a mixing/blending chamber (not shown) where a high-grade biocompatible filler gas can be added as desired in a desired blend formulation.

In certain embodiments, the blending is performed in situ corresponding to the scheduled procedure (and its associated gas formulation) and/or the polarization level of the gas. That is, the hyperpolarizer 10 can be configured with a mixing/blending chamber and a source of biocompatible fluid that will be combined with the polarized gas to provide the blended formulation of pharmaceutical polarized gas product proximate in time and at the production site of the polarized gas itself.

In other embodiments, the receiving container can be pre-filled (and shipped and/or stored) with a high purity medical grade holding gas such as $N_2$ to inhibit the permeation of oxygen therein. The holding gas can form part of the blended formulation or can be expelled prior to dispensing the polarized gas or gas mixture.

In certain particular embodiments, after the polarized gas is cooled to about ambient temperature, a polarization measurement is obtained and the formulated blend volume of unpolarized gas added based on the polarization level to form a controlled blend for more consistent imaging/NMR evaluations procedure to procedure. The blending may be carried out automatically by the hyperpolarizer 10 by controlling the amount of polarized gas and the amount of fluid blending constituent(s) that is released into the mixing/blending chamber or released separately into the dispensing container to provide the formulated blend. See, U.S. patent application Ser. No. 09/949,394, for descriptions of methods and devices for providing meted formulations and amounts of polarized gas, the contents of which are hereby incorporated by reference as if recited in full herein.

Figure 5:
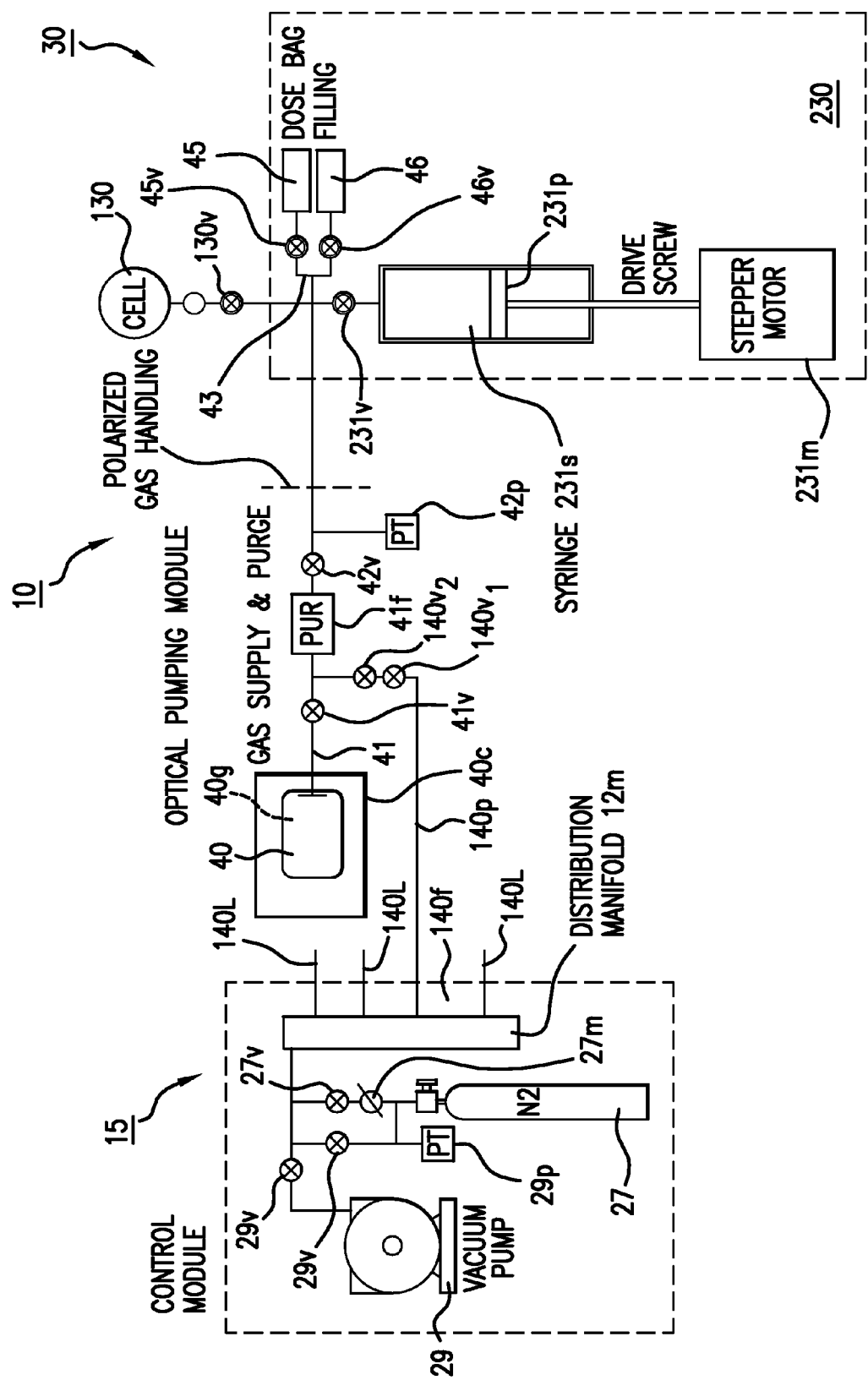
FIG. 5 is a schematic illustration of a hyperpolarization system according to embodiments of the present invention.

FIG. 5 illustrates one embodiment of a hyperpolarizer 10. As shown, the hyperpolarizer 10 includes a control module 15 and an optical pumping module 30. The hyperpolarizer 10 is configured to be able to support or engage with additional optical pumping modules (not shown for clarity of discussion), as discussed above. The control module 15 is in fluid communication with the optical pumping module 30 as noted by the lines 140p extending between and through the two modules 15, 30. The unconnected lines 140l extending from the control module 15 are to connect with additional respective pumping modules (not shown).

The fluid distribution system includes a manifold 12m that is in fluid communication with the purge source 27 and the vacuum pump 29 (located upstream of the manifold 12). As shown, the pump 29 has a valve 29v in line therewith (this valve as shown can be located upstream of the purge source 27). Similarly, the purge source 27 has a flow meter 27f and valve 27v associated therewith and can include a pressure transducer 29p or sensor and valve 29v'. The distribution manifold 12m directs the purge gas and/or vacuum to a desired optical pumping module (shown as module 30). In this way, the vacuum pump and purge gas sources can be shared with other pumping modules. Other valving and plumbing arrangements can be used as will be appreciated by those of skill in the art.

In certain embodiments, the purge source 27 of nitrogen can also be used to blend with the polarized gas to provide the proper dose concentration following polarization.

Still referring to FIG. 5, in certain embodiments, the valves 29v, 27v, and manifold 12m can be configured to actuate via command signals sent from the controller 19. That is, the valves can be hydraulic, pneumatic or air-actuated solenoid components that open and close automatically at the proper time in the production cycle to define a portion of an automated fluid distribution system.

Downstream of the control module 15 is the optical pumping module(s) 30. In certain embodiments, the optical pumping module 30 includes a gas distribution system (plumbing, valves, pressure sensors, and the like) that directs gas in and out of the optical pumping cell and ultimately out of the hyperpolarizer 10 into receiving containers (shown as dose bags 45, 46) via a dispensing system 230 (shown generally by the broken line on the right hand side of the figure).

In operation, prior to polarization, the valve 27v is opened and the distribution manifold 12m activated to select the desired optical pumping module port (shown as 140f) and open the corresponding flow path(s). The gas flow path from the control module 15 to the optical pumping cell 130 is opened so that purge gas is able to flow therethrough. As shown in the embodiment of FIG. 5, valves 140v$_1$, 140v$_2$, 42v and 130v are opened to define the purge gas travel path. The purge gas is evacuated from this path by closing valve 27v and opening valve 29v to evacuate the line. The purge/evacuation steps can be repeated several times. The vacuum in the flow path should be able to reach about 50-100 mTorr. A leak check can also be carried out to assure of proper connections and seals.

As also shown in FIG. 5, the optical pumping module 30 includes an unpolarized gas entry port 41 and associated valve 41v with a filter (oxygen and/or water) 41f located upstream thereof. Similar to the optical pumping cell purge/evacuation procedure, the valve 42v can be closed and valve 41v opened to evacuate/purge this region of the gas flow path prior to introducing unpolarized gas into the system so as to remove oxygen. Valves 140v$_1$, 140v$_2$ and the distribution manifold 12m can be closed after the purge/evacuation portion of the polarization production cycle has been completed (and valves 27v and 29v can also be closed as desired). As before, these valves 140v$_1$, 140v$_2$ and the others shown and described herein can be remotely actuated to open and close at the appropriate time upon the command or control of the control modules 15.

Subsequently (and typically proximate in time thereto), a gas mixture (formulated for operation in the optical pumping cell) can be introduced into the gas port 41 and the next portion of the production cycle commenced. In the embodiment shown in FIG. 5, the unpolarized gas entry port 41 can be configured to receive the pre-packaged meted batch compressible container 40 of polarizer gas mix as discussed above. As shown, the compressible container 40 can be held inside a bag chamber 40c. Upon a secure sealed engagement with the gas entry port 41, the gas 40g can be expelled from the container by compressing the bag. In certain embodiments, fluid can be directed into the chamber 40c to generate the compression force onto the bag 40.

In other embodiments, the valves in the flow path between the gas container 40 and the syringe 231s can be opened and the syringe 231s can be used to draw the gas 40g from the container 40 without requiring external compression of the bag.

In any event, the gas, under pressure, is expelled from the container and directed into the optical pumping cell 130. Valves 41v, 42v and 130v can be opened to direct the gas 40g from the port 41 to the optical pumping cell 130. During active spin-exchange polarization these valves can be closed.

In preparation of dispensing polarized gas, and prior to releasing the polarized gas from the optical pumping cell 130, the polarized gas paths can be purge/evacuated by opening valves 140v$_1$, 140v$_2$, 42v, 231v, and, in turn, closing valve 231v and opening valve 45v and/or 46v.

FIG. 5 illustrates that the gas dispensing system 230 can include a syringe 231s with a plunger 231p. The plunger 231p can be connected to an automated translation device such as a stepper motor or servo with encoder and the like. The stepper motor 231m can be operably associated with the control module 15 so that the stepper motor 231m can automatically draw in or expel polarized gas based on commands sent from the control module at the appropriate time in the production cycle. A carrier fluid (selected to be a constituent of the pharmaceutical polarized gas product) can be directed into the syringe 231s before, after, or concurrently with the introduction of polarized gas. In particular embodiments, after the purge/evacuation is performed, a quantity of high-purity medical grade nitrogen can be pre-filled into the syringe 231s. The nitrogen can be obtained by directing a quantity of the purge gas from the control module 15 into the syringe 231s.

In alternate embodiments, rather than directing the unpolarized gas mixture to the optical pumping cell 130 based on the gas chamber 40c, the unpolarized gas mixture can be dispensed from the syringe 231s. That is, the valves in the fluid distribution system can be operated so that the syringe 231s withdraws the unpolarized gas from its package 40 and then transfers the gas to the optical pumping cell 130 by expelling it from the syringe 231s to introduce the gas into the optical pumping cell 130 under pressure.

Referring to FIG. 5, valves 130v and 231v can be opened to direct the polarized gas in the optical pumping cell 130 to exit and travel to the syringe 231s. The amount (volume) drawn into the syringe (and rate of flow therein) can be controlled by movement of the plunger 231p. Similarly, the volume of carrier fluid (such as nitrogen) drawn into the syringe 231s can be controlled by the position of the plunger as controlled by the stepper motor. The measured volume of polarized gas can be controlled by controlling the position of the plunger 231p in the syringe 231s according to the pressure/volume relationship, or by measuring pressure (with a pressure sensor (FIG. 7)) and controlling the position of the plunger relative thereto or other suitable means. A polarimetry measurement can be obtained proximate in time to opening valve 130v and this information considered when determining the amount of polarized gas needed to form the desired blend.

Not all the polarized gas in the optical pumping cell 130 need be expelled or directed into the syringe 231s at once. Rather, the syringe 231s can be filled (or partially filled) a plurality of times using one batch of polarized gas. When the desired amount of polarized gas has been drawn into the syringe 231s, valve 130v can be closed. The process can be repeated until all the polarized gas has been used. Different carrier fluids may be added to selected dose formulations while other dose formulations can employ only the polarized gas. Similarly, different amounts of carrier fluid can be added to the blend for various of the doses produced by a single batch depending on the intended use (NMR or MRI procedure and/or body region to be evaluated), the polarization level, and the like.

In certain embodiments, the carrier gas can be introduced into the container dose bag 45, 46 separately from the polarized gas. For example, the syringe 231s can admit nitrogen alone and then direct it to the dose bag 45. Then polarized gas can be directed into the syringe 231s and then directed into the dose bag 45. Hence, the mixing can occur in the dose bag 45 itself.

Prior to directing gas into the receiving container(s) 45, 46, valve 231v can be closed and the purge/evacuation process performed on the gas dispensing ports (and associated containers 45, 46 as desired if not performed prior) by opening valve 42v, the valve associated with the dispensing port 43 (shown as one of valves 45v and 46v), so that the purge gas can flow from the control module 15 to the optical pumping module when valves $140v_1$, $140v_2$, 42v, 45v and/or 46v are open. Then, valve 42v and upstream valves can be closed (as is valve 130v) and valve 231v can be opened to direct the polarized gas (or gas mixture) from the syringe 231s to the gas dispensing port 43 and into the selected container 45 or 46.

Figure 6A:
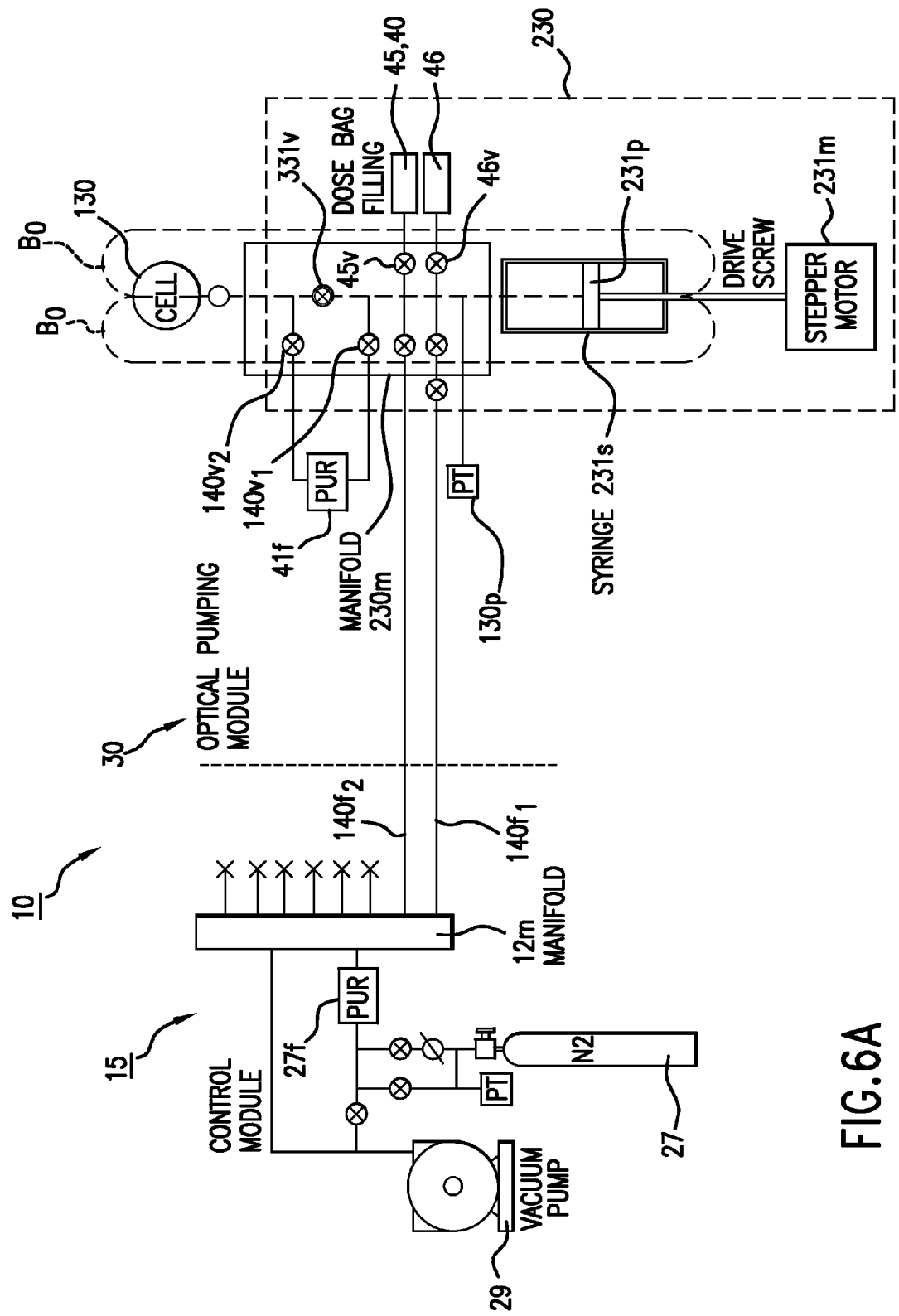
FIG. 6A is a schematic illustration of another hyperpolarization system according to embodiments of the present invention.

FIG. 6A illustrates another embodiment of a hyperpolarizer 10 similar to that shown in FIG. 5. In this embodiment, the dose bag or bags 45, 46 can be used to supply the prepolarized gas 40g mixture (not requiring a separate gas input port like that shown in FIG. 5). As shown in 6A, there are two fluid connections $140f_1$, $140f_2$ extending between the control module 15 and the optical pumping module 30. One can be used for the nitrogen gas supply line $140f_1$ (for purge and dose mixing operations) and the other for the vacuum for the purge/vacuum noted above.

In certain embodiments, the system 10 can be configured so that, in operation, nitrogen flows through the line $140f_1$ via a regulator and a purifier in the control module 15 to the optical pumping module 30. As the nitrogen enters the pumping module 15, it can be directed to pass through an orifice to control the flow rate. The nitrogen then encounters an air pilot operated valve. The nitrogen supply can be used during purge procedures and to blend with the polarized gas for mixing/dilution as desired. The mixing/dilution may be particularly suitable for preparing polarized $^3$He formulations. A separate vacuum line $140f_2$ can be used so that the vacuum does not have to be pulled through an orifice or small valve opening. The pilot control fluid or air-line(s) are not shown (to form the pneumatic or hydraulic connection for remote automated actuation of the valves).

In this embodiment, the unpolarized gas can be supplied at the gas dispensing port 43; that is, the gas inlet and the gas outlet port are the same. In certain embodiments, the unpolarized gas supply bag can be used both as the unpolarized gas supply container and the polarized gas dose bag. In any event, the unpolarized gas is withdrawn from the container 40 into the syringe 231s and is directed into the optical pumping cell 130 at a selected elevated pressure (such as between 1-8 atm) using the syringe 231s. The syringe 231s is also used as noted above to form the polarized gas measured (dose) amount to the container or dose bag 45 (or 46). The magnetic field $B_0$ is generated so as to provide a homogeneous magnetic field for the optical pumping cell 130, the syringe 231 and the manifold or plumbing therebetween so that the polarized gas is held in the magnetic field during production and dispensing. Examples of the magnetic field flux lines are illustrated as broken lines in a symmetric elongated oval pattern about the center of the field. The receiving container or dose bag 45 and/or 46 may have its own magnetic field, or the magnetic field may be generated so that it also covers these components during dispensing. The homogeneous magnetic field may be configured to provide about dB/B of less than about 0.001 cm$^{-1}$ for those portions of the system where polarized gas will reside for any substantial length of time, such as above about 1 hour, like in the main body of the optical pumping cell itself. In other portions of the system, such as where the polarized gas will be flowing, but not sitting for any substantial length of time, a homogeneity of less than about 0.01 cm$^{-1}$ may be sufficient.

As shown, a pressure sensor such as a pressure transducer (labeled PT) can be located proximate the entry or exit port of the syringe. A different flow path can be used to deliver the unpolarized gas to the optical cell from the syringe compared to the one used to deliver polarized gas back to the syringe after polarization. For example, prior to polarization, the fluid distribution system and optical pumping cell 130 can be prepared (purge/evacuated) as noted above. The small circle in front of the cell 130 illustrates a manual valve that can have a normally open position and is typically closed for installation and replacement. In any event, valve 331v can be closed, and valves $141v_1$ and $141v_2$ opened so that the unpolarized gas exits the syringe 231s under pressure, and travels through the plumbing leg of the fluid distribution system that has the filter 41f before it enters the optical pumping cell 130. After polarization, valve 331v can be opened and valves $141v_1$ and $141v_2$ closed so that the polarized gas goes directly to the syringe 231s thereby reducing the post-polarization travel distance of the polarized gas to the syringe 231s from the optical pumping cell 130 compared to the unpolarized gas travel distance from the syringe 231s to the optical pumping cell 130. This travel path also diverts the polarized gas so that it does not travel through the filter 41f.

As noted above, the dose concentration and/or polarization gas volume can be controlled by the position of the plunger in the syringe and/or the pressure measurement obtained by the pressure transducer according to basic gas laws (PV=nRT).

Figure 7:
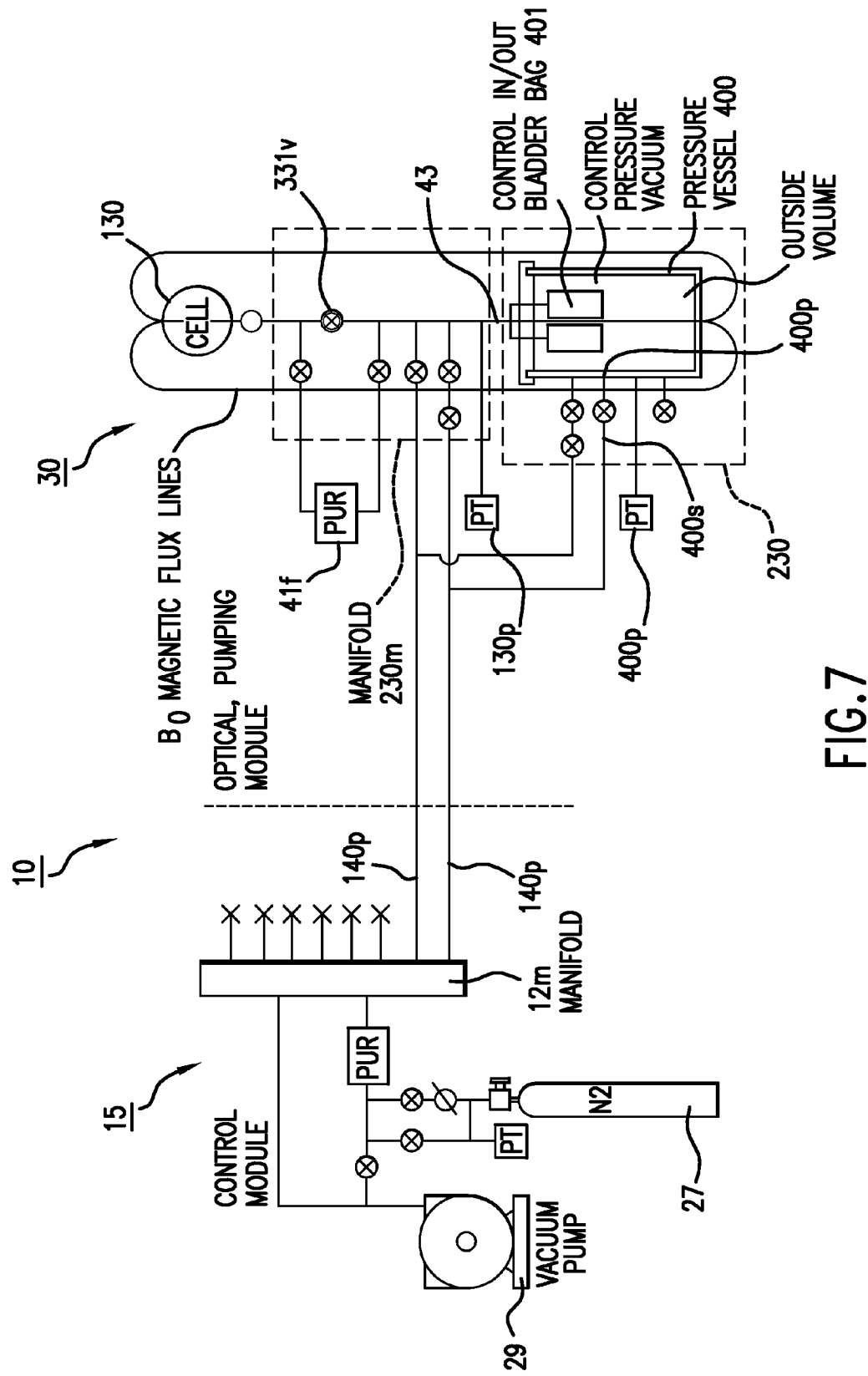
FIG. 7 is a schematic illustration of a hyperpolarization system according to additional embodiments of the present invention.

FIG. 7 illustrates an additional embodiment of a hyperpolarizer 10. In this embodiment, a pressure tank 400 is used with the same port 43 for filling and dispensing. A supply of unpolarized gas can be introduced into the tank in one or more compressible (flexible or resilient) bags 401. The tank 400 can be closed. As before, the system or portions thereof can be purged/evacuated. The tank 400 can be in fluid communication with a fluid supply 400s (which can be the nitrogen or purge gas) that is allowed to enter or leave the tank via port 400p. The tank is pressurized by controlling the volume of the fluid introduced into the tank 400 so that the bag(s) 401 are compressed with a desired pressure to force the unpolarized gas mixture from the bag(s) to enter the optical pumping cell 130 under pressure. As described for the embodiment of FIG. 6A, a different flow path can be used to direct the unpolarized gas into the cell 130 compared to the path the polarized gas takes back to the bag(s) 401 in the tank 400 after polarization. The gas is then polarized in the optical pumping cell 130.

The pressure in the flow path can be measured as well as the pressure in the tank 400. As shown, the pressure in the tank 400 is measured by pressure sensor 400p and the pressure in the fluid distribution system (and hence optical pumping cell) is measured by pressure sensor 130p.

The pressure in the tank is reduced and the polarized gas then is directed back into the supply container(s) 401. If more than one container is employed, the bags can be filled either concurrently or serially. Nitrogen or another carrier fluid can be introduced into the bag 401 to blend the polarized gas to the appropriate formulation as described above. In particular embodiments, the carrier fluid is placed in the bag 401 after the gas is expelled from the container to the optical pumping cell 130 and prior to allowing the polarized gas to re-enter same. This can be carried out by closing valve 331v and opening the purge source line (typically after the purge/evacuation procedure). The volume of nitrogen or other carrier gas in the formulated polarized gas product can be measured and controlled by monitoring the pressure change in the tank while inflating the supply containers with nitrogen or other carrier gas. The pressure change corresponds to the amount of nitrogen or other carrier gas in the bag. The amount of polarized gas can be controlled by monitoring pressure using sensor pressure 400p. Once nitrogen is dispensed into the bag, a new base line pressure can be read and the polarized gas, such as $^3$He gas can be dispensed. The polarized gas can be polarized, handled, and dispensed into the container 401 within a homogeneous magnetic field.

Figure 8A:
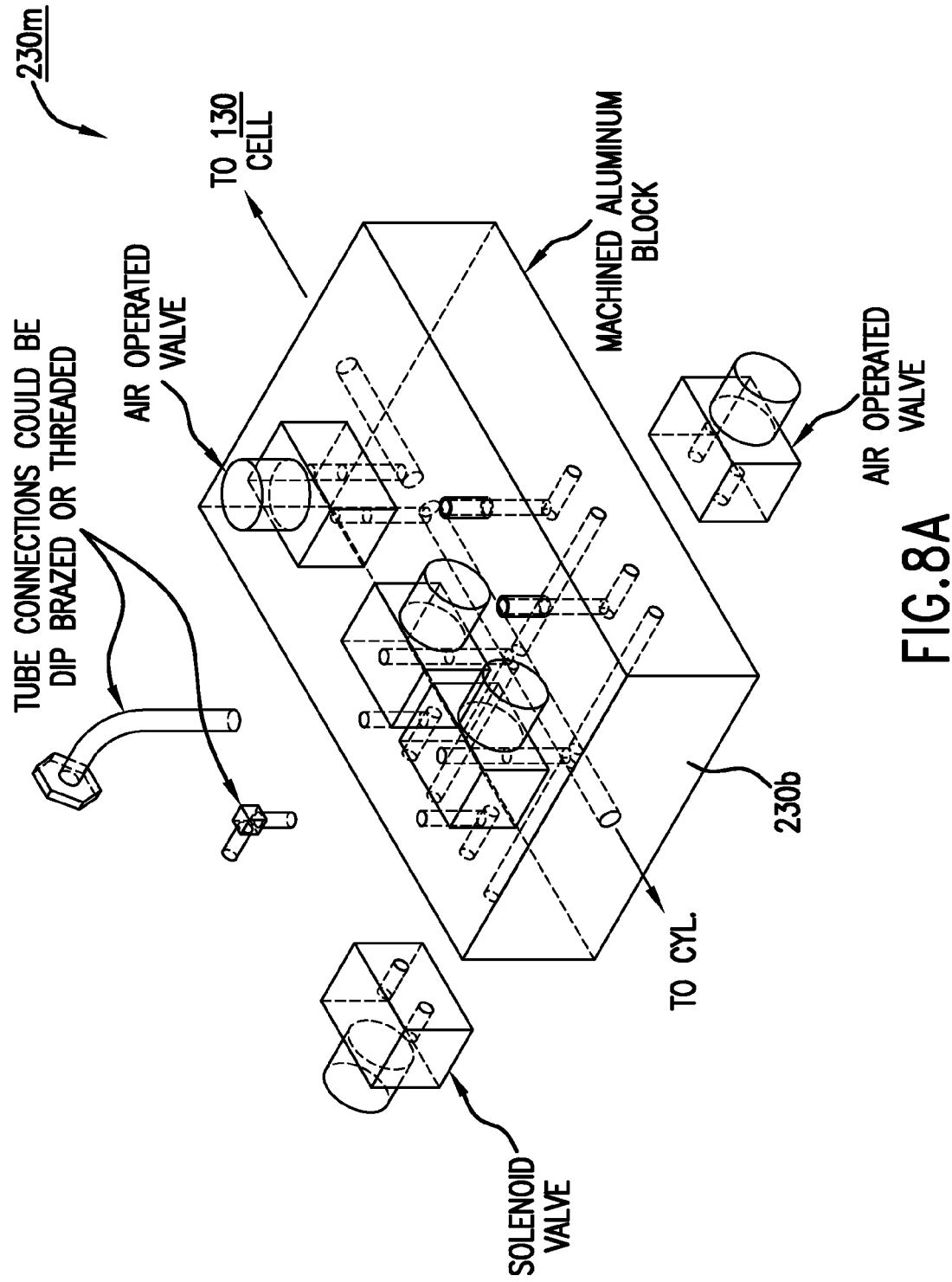
FIG. 8A is a schematic illustration of a fluid distribution manifold according to embodiments of the present invention.
Figure 8J:
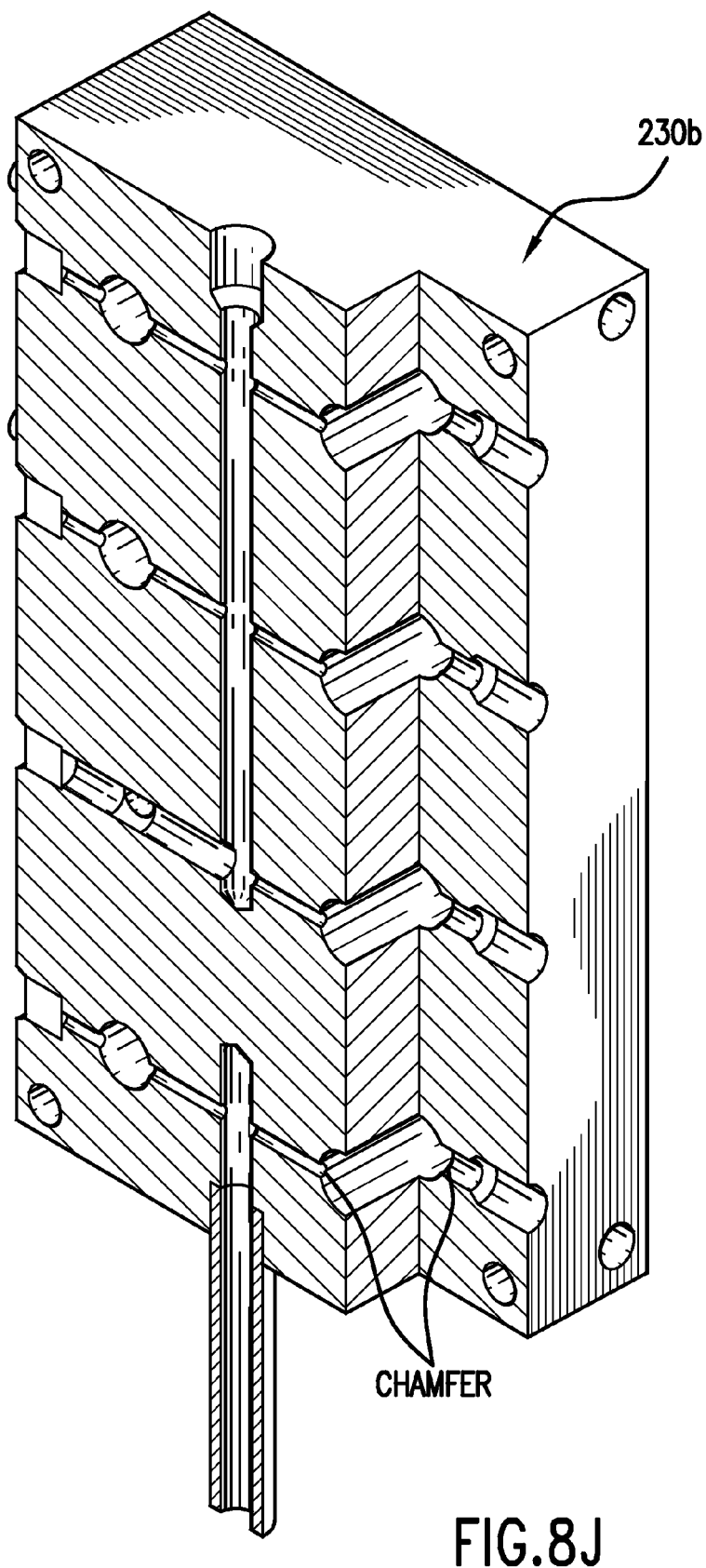
FIG. 8J is a partial cutaway view of a housing without valves corresponding to the device shown in FIG. 8B according to embodiments of the present invention.
Figure 8K:
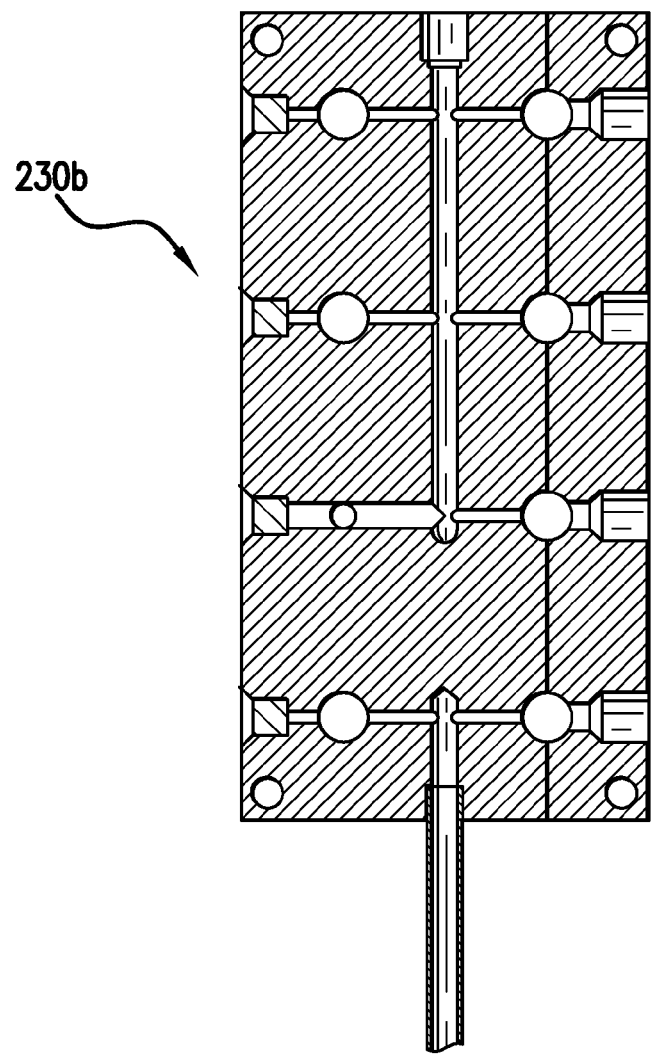
FIG. 8K is a section view taken along the device shown in FIG. 8J according to the direction of the section line and arrows shown.
Figure 8K:
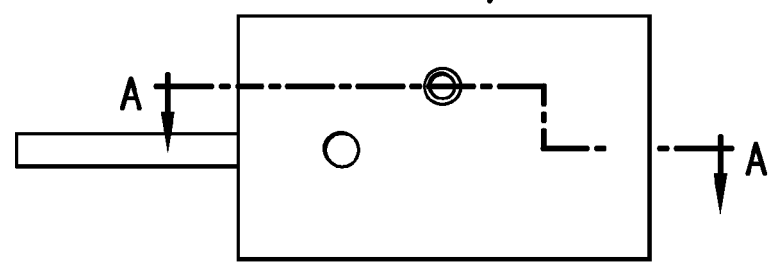

FIG. 8A shows one embodiment of a fluid distribution manifold 230m that can form a portion of the fluid distribution system for a hyperpolarizer 10 according to the present invention (for clarity it is noted that the embodiment shown in this figure does not correspond to any of the examples of schematics discussed previously). As shown, the manifold 230m can be a block 230b having a plurality of gas flow paths formed therein. The block 230b can be an aluminum-machined block that can support pneumatic pressures and, for the gas flow path, form polarized gas friendly (high purity, substantially free of paramagnetic impurity) contact surfaces. See U.S. Pat. Nos. 6,128,918 and 5,612,103 for further description of suitable materials and coatings, the contents of which are hereby incorporated by reference as if recited in full herein. The manifold 230m can include a plurality of separately selectable gas flow paths therein.

Figure 6B:
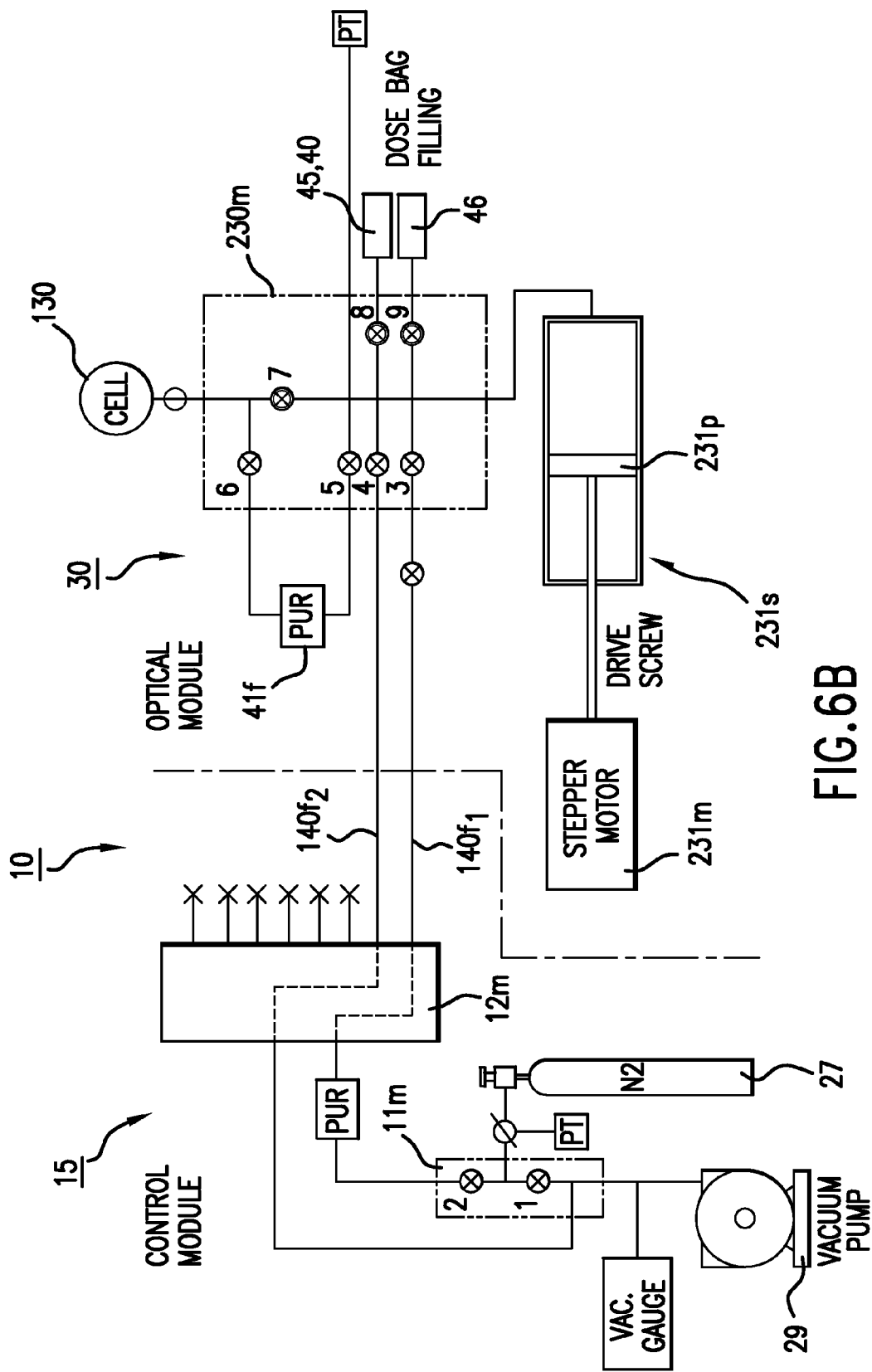
FIG. 6B is a schematic illustration of an embodiment similar to that shown in FIG. 6A, but with the syringe oriented in a different direction, and with the valves labeled as numbers 1-9 to correlate with those shown in example manifold assemblies shown in FIGS. 8B-8I.

FIGS. 8B-8K illustrate examples of manifold assemblies that can form a portion of the flow path, these figures correspond to the system shown in FIG. 6B. Other configurations can be produced to provide the other system connections and operations as desired. Referring first to FIG. 6B, this figure illustrates an embodiment of a system similar to that shown in FIG. 6A, but with the syringe 231s oriented in a different direction. For ease of description, the valves in FIG. 6A have been renumbered as components 1-9. These numbers correspond to valve identifiers used in FIGS. 8B-8K so that their operation and location relative to the system 10 are more clearly described. The valves can be configured to operate in the 15-180 psig range. Suitable valves are available from FABCO.

FIGS. 8B-8E illustrate a manifold assembly 230m in the optical pumping module 30 that holds valves 3, 4, 5, 6, 7, 8, and 9 thereon. The manifold assembly housing block 230b is illustrated without the valves in FIGS. 8J and 8K. In operation, the inlet side is identified as the side of greatest pressure but may not necessarily be the typical direction of flow (indicated by the arrows). FIGS. 8F-8I illustrate an example of one manifold assembly 11m in the control module 15. This manifold can be configured as a nitrogen manifold with valves 1, 2 thereon.

Figure 9B:
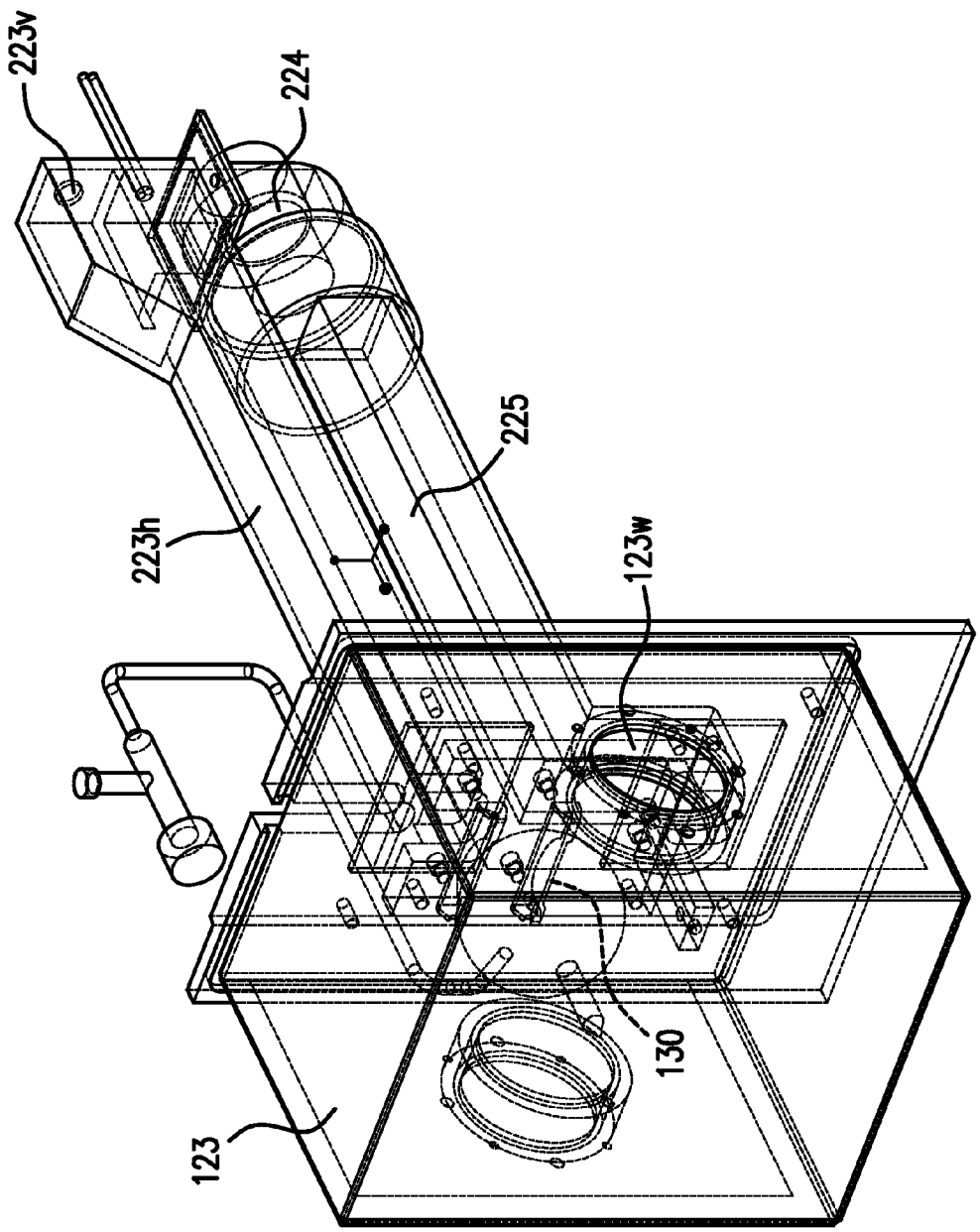
FIG. 9B is a side perspective view of the device of FIG. 9A illustrating internal components according to embodiments of the present invention.
Figure 9C:
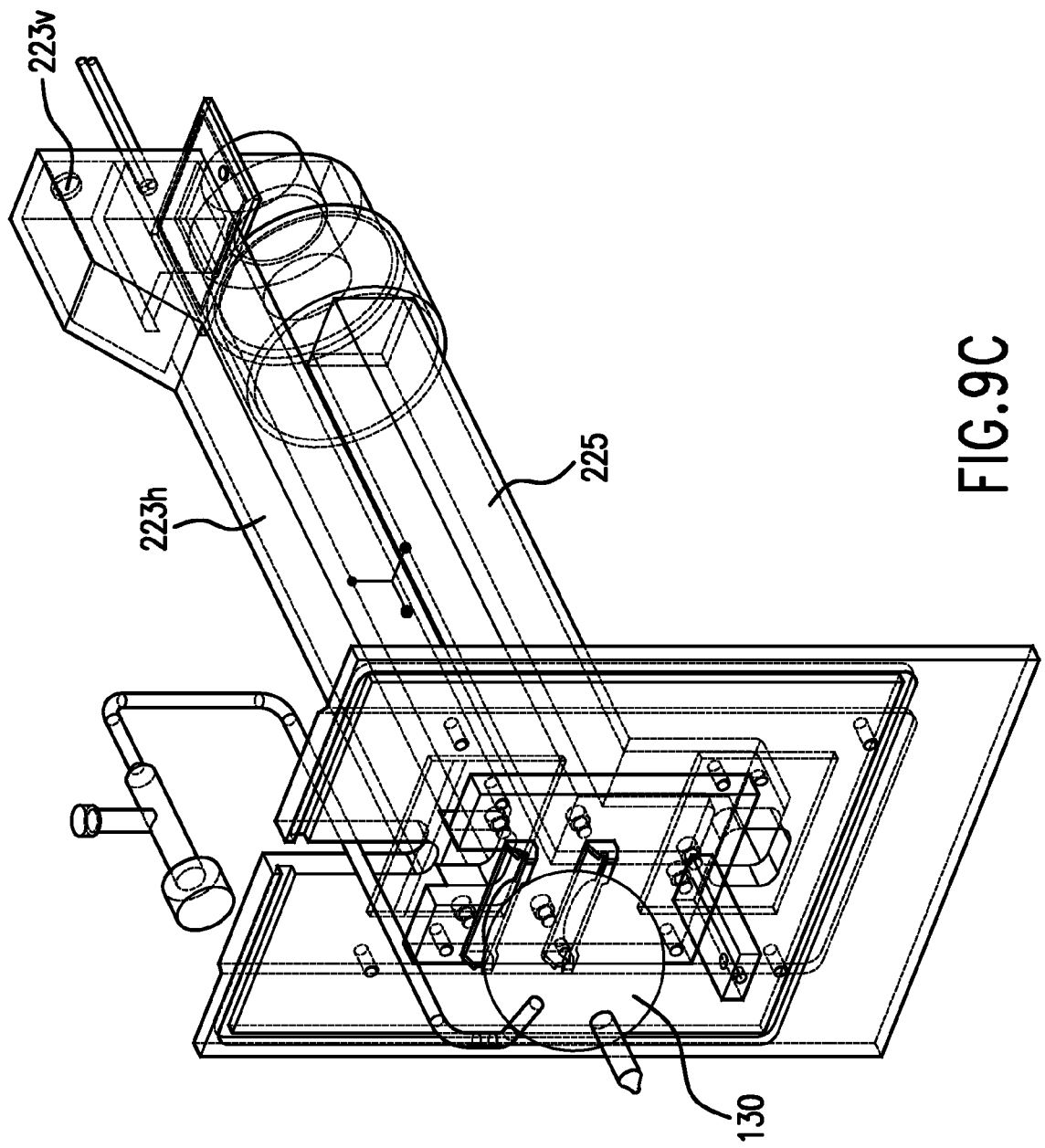
FIG. 9C is a side perspective view of the device of FIG. 9B with the oven enclosure removed according to embodiments of the present invention.

FIGS. 9A-9C illustrate an optical cell thermal assembly 223. The assembly 223 includes the oven 123 that encases the optical pumping cell 130 (FIGS. 9B and 9C). The oven includes a laser window 123w formed therein that allows the laser light to enter the optical pumping cell. The assembly 223 also includes an elongated housing extending from the oven to an axial distance away therefrom. FIG. 9B illustrates that the housing 223h has a cool air venturi 223v formed therein. The assembly 223 also includes a heating element 225 that supplies the heat to the oven 123 and a fan 224 disposed in the housing 223h at an end portion away from the oven 123 (upstream of the heating element 225) so that it is in fluid communication with the heating element and the cool air venturi. In operation, the oven 123 is configured to have a temperature of between about 150-200° C. The optical cell thermal assembly 223 is configured to have a substantially closed thermal system to reduce the power requirement or "on" time of the heating element by harnessing the laser energy. That is, the heating element supplies sufficient energy to vaporize the Rb in the optical cell 130. Once the Rb is vaporized, the laser energy can be captured by the Rb and dissipated as heat. The temperature in the oven is maintained by the captured heat dissipation. Small adjustments in temperature can be made by a temperature controller. The controller 120 (FIG. 3B) can activate the heating element 225 or air venturi 223v depending on whether the temperature is below or above a desired value. Then, following optical pumping, the venturi 223v is used to quickly cool the oven 123 and the cell 130. This is done to remove the Rb from the polarized gas (typically helium) through condensation. Performing the cooling quickly may allow for optimum or increased polarization upon dispensing.

In certain embodiments, when obtaining polarimetry measurements, the $T_2^*$ value can be in excess of about 5 ms (an example of a mute time after the pulse is transmitted is about 3 ms, but this value can be otherwise), although the $T_2^*$ value may be increased above this value depending on the system configuration and/or magnetic field configuration. This means that for a hyperpolarizer unit 10 with a magnetic field $B_0$ generated by an optical pumping module with an integrated "on-board" 6-19 inch diameter Helmholtz coils, the coils are positioned and configured to generate a region of homogeneity which is defined by a virtual cylinder having a length of less than about 2 inches and a radius of less than about 2 inches centered between the coils (with the optical cell 130 being located in the homogeneous region created thereby)).

In other embodiments, the magnetic field $B_0$ is generated by a solenoid magnetic field source. The solenoid can be configured as an end compensated solenoid to flatten out and extend the homogeneous field as described in U.S. patent application Ser. No. 09/333,571, the contents of which are incorporate by reference as if recited in full herein. The solenoid can provide increased regions or volumes of homogeneity or that conventionally provided by Helmholtz coils. In certain embodiments, the solenoid can be sized and configured with about a 10-12 inch diameter. The cylindrical solenoid may also be configured to be about 20-60 inches long or even longer, and typically can be about 40 inches long.

Lists of exemplary operational pressures and function for the valves shown in FIGS. 8A and 8F are provided below.

FIG. 8A

| Valve (3) | Nitrogen-UHP (Purge) | INLET: Vac. 110 psig |
| | | OUTLET: Vac. 15 psig |
| Valve (4) | Vacuum (Evacuate) | INLET: Vac. 110 psig |
| | | OUTLET: Vac. 15 psig |
| Valve (5) | Purifier (Purifier IN) | INLET: Vac. 110 psig |
| | | OUTLET: Vac. 110 psig |
| Valve (6) | Fill (Cell IN) | INLET: Vac. 180 psig |
| | | OUTLET: Vac. 110 psig |
| Valve (7) | Dispense (Cell OUT) | INLET: Vac. 180 psig |
| | | OUTLET: Vac. 110 pig |
| Valve (8) | Dose Bag 1 (3He Outlet 1) | INLET: Vac. 110 psig |
| | | OUTLET: Vac. 15 psig |
| Valve (9) | Dose Bag 2 (3He Outlet 2) | INLET: Vac. 110 psig |
| | | OUTLET: Vac. 15 psig |

FIG. 8F

| Valve (1) | Vacuum Reg. (Evacuate Reg) | INLET: Vac. 15 psig |
| | | OUTLET: Vac. 15psig |
| Valve (2) | Purge line (Purge shut-off) | INLET: Vac. 15 psig |
| | | OUTLET: Vac. 15 psig |

The tubing used to connect the pressurizing/mixing syringe and/or the pressure transducer to the manifold 231*m* may be aluminum and ultra-Torr fittings may be employed for the dose bag channel connections to the manifold.

In operation, when obtaining polarimetry measurements of the polarized gas, the oven temperature can be measured or obtained (based on known controlled operation) because at high temperatures the gas density will be reduced according to the relationship expressed by the ideal gas law (PV=nRT). For example, if the oven 123 is set to operate at 150° C., the density of xenon is about (295K/423K or 0.70) of the room temperature density. The signal associated with the hyperpolarized gas when measured at room temperature versus greatly elevated temperatures can be reduced correspondingly.

Figure 4A:
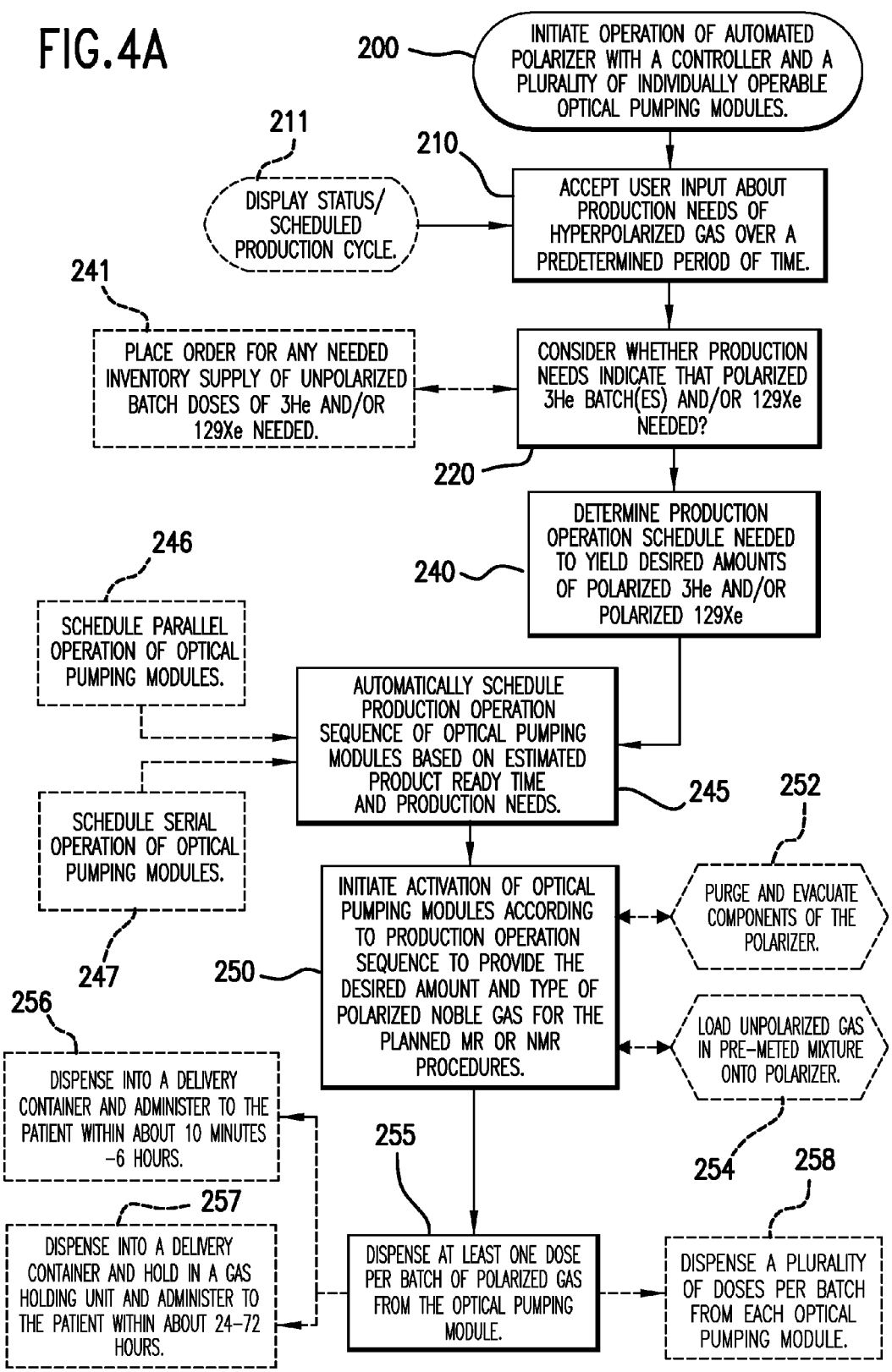
FIG. 4A is flow diagram of operations of a hyperpolarizer according to embodiments of the present invention.

FIG. 4A illustrates examples of operations according to embodiments of the present invention. As shown, operation of an automated hyperpolarizer having a central controller and a plurality of optical pumping modules can be initiated (block 200). The hyperpolarizer can accept user input regarding the number of procedures, the type of procedure scheduled and the days and times of the scheduled appointments over a selected period of time (block 210). The user input may indicate whether the planned procedure is for NMR or MRI evaluation (or both). For example, the scheduled procedure can be correlated to the quantity and type of polarized gas or gas formulation that is needed to support the procedure. This may include one or both injected or inhaled formulations and quantities, and the amount may depend on whether the procedure will be for ventilation (typically static), dynamic imaging or signal analysis, oxygen diffusion/perfusion mapping, dynamic with oxygen mapping or perfusion. The procedure can also indicate what is the targeted region to be evaluated, such as, but not limited to, the pulmonary system, the cardio-pulmonary system, the cerebrum or brain, or another other organ, system, or region of interest. Information regarding the scheduled procedure can be used to generate an estimated associated polarized gas amount and type needed to support the planned evaluation.

In certain embodiments, the system can display the operational status and production cycle and/or schedule that is planned for the hyperpolarizer (block 211). This information can also be monitored remotely via a computer or wireless link (to the facility or clinic or a remote service station). Thus, when there is a discrepancy between production capacity and need, an alert can be generated so that remedial steps can be taken in advance of the appointment of the patient to avoid NMR/MRI system downtime. This can be to reschedule the patient, obtain additional supplies of polarized gas from a different source, and the like.

The production data can be reviewed to determine whether one or both polarized $^3$He and $^{129}$Xe are needed (block 220). The system can also be configured to track an inventory supply of unpolarized production run or batch amounts of $^3$He and $^{129}$Xe that may be needed to support the production schedule and indicate that orders for additional amounts are needed (and when) (block 241). The batch amounts of $^3$He and $^{129}$Xe can be supplied as pre-mixed and pre-packaged formulations of blends to provide single production run blends in convenient production kits (that can have a shelf life of up to about 6 months) and indicate whether and when additional batch kits are needed.

The system can be configured to project or forecast a production schedule and need requirement that can be periodically re-evaluated (such as daily or even more often). The production operation schedule can be determined that can provide the desired amounts of polarized $^3$He and/or $^{129}$Xe (block 240). That is, the time it takes to produce a batch of the desired type of polarized gas is estimated and the time that the doses are required are known as well as the life expectation limits of same. The system can be configured to compute one or more production schedules to meet the production demand and the life expectancy of the polarized gas.

In addition, a reserve supply of polarized gas can be generated for each 12 hour period; however, it is anticipated that this amount will be limited to control costs as the product if unused within a reasonable time will be wasted. In addition, if the reserve is depleted, the immediate or current day supply production run period (0-12 hours) and a subsequent period can be revised to allow for a reserve supply to be generated. In other embodiments, the production schedule is re-evaluated every 6-48 hour period, so that the production run schedule yields the desired amount of polarized gas for the next 24-48 hours, 24-72 hours, or other time interval period. For example, if there are no procedures planned for Day 0, the current day, four MRI procedures planned for Day 1, and 5 MRI procedures planned for Day 2, and the production capacity is 3 production runs per day (per 8-12 hour period), then either the polarizer can run at full capacity on Day 0 and a second shift can be scheduled to run the hyperpolarizer on either Day 1 or Day 2. Of course, other adjustments can also yield the desired production volumes.

The hyperpolarizer can be operated to automatically schedule the production operation sequence of the optical pumping modules based on estimated product ready time (per batch) and the production need (patient delivery/appointment time) (block 245). The optical pumping modules can be scheduled to operate in parallel (block 246) or in series (block 247). That is, the optical pumping modules can have staggered start times with overlapping periods of operation or operate serially one after the other is completed. Activation of the optical pumping modules can be initiated according to the production operation sequence schedule to provide the desired amount and type of polarized gas for the planned MRI or NMR procedure (block 250). The system can purge and evacuate certain components of the polarizer (block 252) prior to initiate of the polarization. In addition, the unpolarized gas mixture (in a meted pre-packaged amount) can be loaded into the optical pumping module (block 254).

At least one dose of polarized gas per production run or batch can be dispensed from the optical pumping module (block 255). In certain embodiments, a plurality of doses per batch can be dispensed from each optical pumping module (block 258). The dose can be dispensed into a delivery container and administered to the patient within about 10 minutes to 6 hours (block 256). In other embodiments, the dose can be dispensed into a patient delivery receptacle or container and held in a gas holding chamber or unit to be subsequently administered to the patient within about 24-72 hours from dispensing (block 257). The container can include a label with the polarization measurement and time taken or with a projected shelf-life use time.

Thus, the polarization can be carried out in a "just-in-time" format, or so that limited storage (typically within about 24-72 hours of dispensing) of the polarized gas is required. Longer storage times can be used in certain applications. However, both polarized $^{129}$Xe and $^3$He have a limited clinically useful polarization life. The polarization life depends on a number of factors, including surface-induced relaxation mechanism. For example, the collisions of gaseous $^{129}$Xe and $^3$He with container walls ("surface relaxation") have historically been thought to dominate most relaxation processes. Another relaxation mechanism is the relaxation due to EMI and oscillating magnetic fields. Unfortunately, EMI can be generated by relatively common sources; as such, transport away from the hyperpolarized gas production site can expose the hyperpolarized gas to these undesirable relaxation sources which, in turn, can dramatically reduce the polarization life of the transported gas (i.e., the $T_1$). For example, EMI is typically generated from a vehicle's engine, high voltage lines, power stations and other current carrying entities. Still another relaxation mechanism is magnetic gradient relaxation that involves the relaxation attributed to the exposure of the hyperpolarized noble gases to inhomogeneous static magnetic fields. Generally stated, as the polarized gas atoms diffuse or move through an inhomogeneous magnetic field, they experience a time-dependent field, which can introduce depolarizing activity onto the hyperpolarized atoms. See U.S. Pat. No. 6,269,648 for additional description of relaxation mechanisms and for a description of shielded transport and storage containers or chambers, the contents of which are hereby incorporated by reference as if recited in full herein.

Figure 4B:
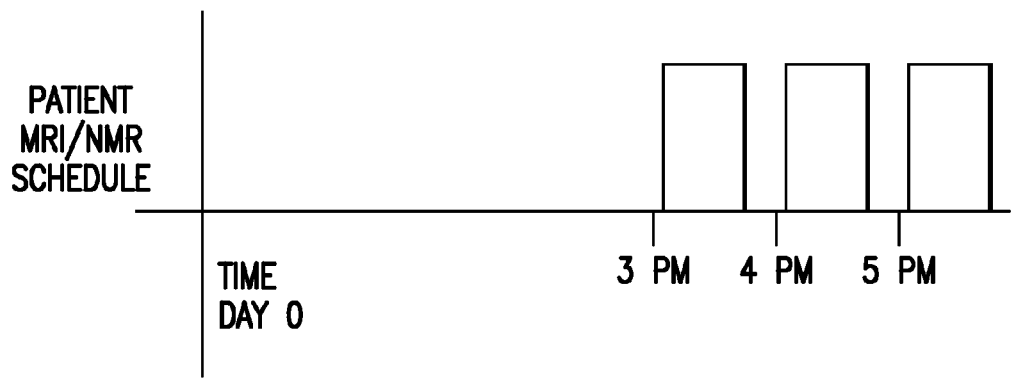
FIG. 4B is a timing graph of patient procedures and FIGS. 4C and 4D are examples of corresponding schedules of production runs of optical modules according to embodiments of the present invention.
Figure 4C:
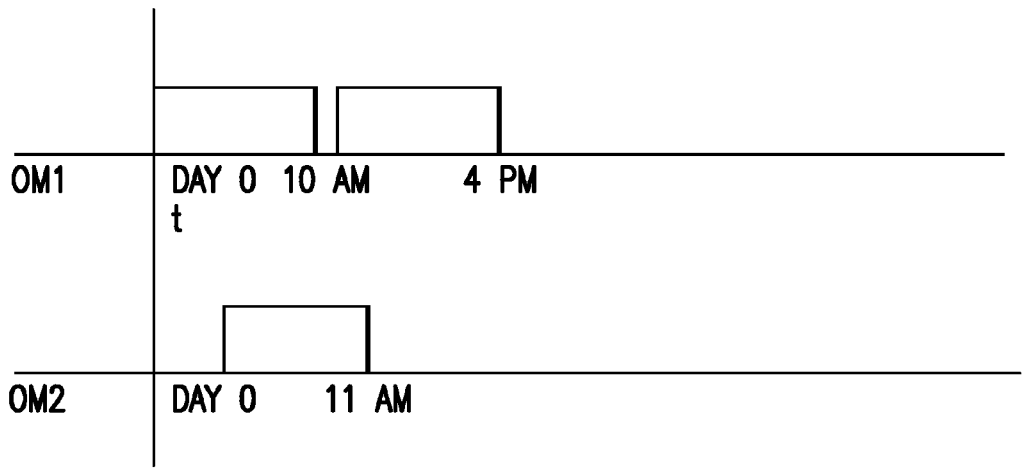

FIG. 4B illustrates the MRI/NMR equipment schedule for patient evaluations using polarized gas. As shown, the procedures may be clustered together to reduce any equipment set-up adjustments needed to run the polarized gas evaluations. Thus, in this example, there are three different procedures scheduled, one each at 3 pm, 4 pm, and 5 pm. FIG. 4C illustrates the production sequence for the optical modules 1 (OM1) and 2 (OM2) that may be used to provide the polarized gas. As shown, OM1 provides two batches of polarized gas, one being ready at 10 am and the other at 4 pm. OM2 provides one batch, available at 11 am.

Figure 4D:
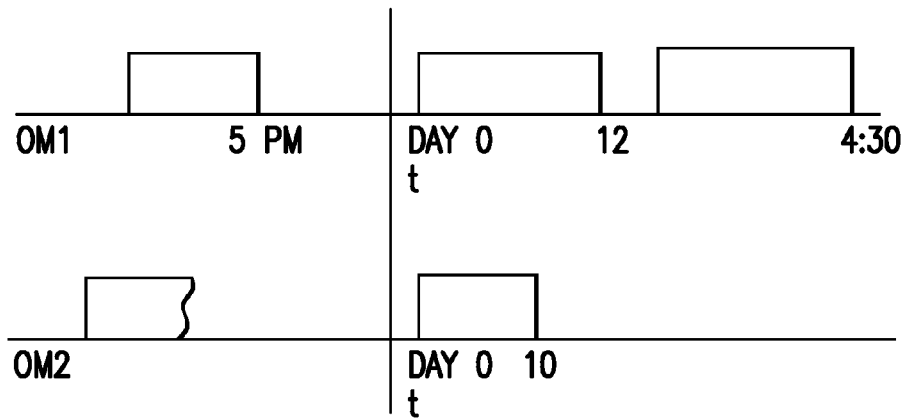

FIG. 4D illustrates another potential schedule sequence. That is, OM1 produces one batch of polarized gas the day before the planned use day (shown as ready at 5 pm). OM2 is shown as also initiating a polarization the previous days, but the procedure having shut down prematurely. Then on Day 0, the day of the planned procedures, OM1 produces two additional batches while OM2 again is running and produces one batch.

FIG. 11 illustrates one potential distribution system according to an embodiment of the present invention. As shown in FIG. 11A, one or more hyperpolarizers 10 can be located at a central or regional polarization facility (or on a transportable based system such as a truck or bus mobile unit) and polarized gas can be dispensed into a gas container (not shown), which is then held in a shielded gas transport unit 245. The gas container can be formed as a cavity in the gas transport unit 245 or can be a separate container. The sequence of operations is indicated by the direction of the arrows in the figures.

As shown in FIG. 10B, the gas transport unit 245 shields the gas during transport from the central or regional facility and delivers the polarized gas to the hospital or clinical site in the vicinity of the MRI or equipment suite. FIG. 10C illustrates that the gas transport unit 245 (with the polarized gas held therein) can be placed in a gas holding or storage chamber 249. The gas transport container 245 and/or the gas holding chamber 249 can be configured to obtain polarimetry measurements to ascertain the polarization level of the gas. As shown, the gas transport container can include a polarized gas release port 245*p* that aligns with the holding chamber gas release port 249*p* so that the polarized gas can be released in situ through both devices into a patient delivery container 145 (shown as a collapsible bag). The delivery bag is then filled (FIG. 10D) and used to administer the polarized gas to the subject during the procedure (FIG. 10E). The delivery bag can then be disposed (single-use disposable container) (FIG. 10F1) and the gas transport container returned to be used again (FIG. 10F2).

FIG. 11 illustrates another embodiment of a distribution system according to the present invention. As shown in FIG. 11A, in this embodiment, one or more central or regional unpolarized gas filling facilities can be used to produce pre-packaged into a container 40 in blended or meted amounts of the target noble gas to be polarized and other constituents in the desired production formulation suitable for polarization in the optical pumping modules. The container 40 can be configured to hold the gas under increased pressure (to be able to expel the gas as an aerosol) or to hold the high-purity gas mixture in an unpressurized state. In certain embodiments, the container is configured so that provides an unpolarized gas shelf life of between about 1-6 months. As shown by FIG. 11C, the hyperpolarizer 10 can be located at the point of use site (hospital or clinic) typically in the vicinity of or proximate to the MRI or NMR equipment. That is, the hyperpolarizer 10 can reside adjacent the MRI suite or in a room of a wing proximate thereto so as to limit the spatial transport and potential exposure to undesirable environmental conditions. In certain embodiments, the polarized gas transport time between the hyperpolarizer and the imaging suite is less than about 1 hour. Placing the hyperpolarizer in the clinic or hospital allows for short and consistent transport times procedure to procedure. In addition, formulating the pharmaceutical polarized gas with a polarized gas having higher levels of polarization can reduce the amount of the polarized gas used to form the end dose product thereby potentially reducing the cost of the product.

As indicated by the broken lines around the pre-packaged container 40 of unpolarized gas mixture 40*g* and the patient delivery device 145, the two components can be shipped as a part of a production batch kit 313 that includes one or more patient delivery containers with the unpolarized gas mixture. The patient delivery container 145 can be shipped partially filled with a biocompatible fluid such as nitrogen. After polarization, the polarized gas is dispensed into the patient delivery container 145 and then either directly administered to the patient (FIG. 11E) or held in a gas holding chamber 249' that can be configured to obtain polarimetry measurements (FIG. 11D). As such, the gas holding chamber can operate as a type of "calibration" station. Prior to use, the polarization reading of the gas can be obtained and this information used to calibrate the signal strength of the NMR data of the polarized gas in the patient during the evaluation session. The container 145 may be configured with an integrated NMR excitation coil and lead wire that can be engaged with the gas holding chamber polarimetry system (not shown). Again, the containers from the kit 313 can be discarded after a single use.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method of providing polarized noble gas for NMR or MRI applications, comprising:

expelling an unpolarized gas mixture comprising a noble gas to be polarized from a pre-packaged container into a hyperpolarizer having an unpolarized gas receiving port, a control module, a plurality of optical pumping modules each including an optical pumping cell operably associated with the control module; a plurality of dispensing systems, one for each optical pumping module wherein each dispensing system is operably associated with the control module and the its associated optical pumping module to dispense meted volumes of polarized gas from the hyperpolarizer, the optical pumping modules, and the dispensing systems, and a polarized gas dispensing port;

directing the expelled unpolarized gas mixture to a selected one of said optical pumping modules;

polarizing the noble gas via spin-exchange interactions with an alkali metal in the selected one of the optical pumping cell of the hyperpolarizer;

heating the noble gas during the polarizing step;

cooling the polarized gas after the polarizing step;

automatically blending in situ the polarized noble gas with a biocompatible fluid to provide a pharmaceutical grade polarized noble gas product suitable for in vivo administration to a subject;

dispensing the polarized noble gas product through the fluid dispensing system associated with the selected optical pumping module into a patient delivery container; and measuring the polarization level of the noble gas;

wherein the measuring step is carried out so as to obtain a reading after the cooling step, and wherein the blending step is a based on the polarization level of the polarized gas after the cooling step.

2. A method according to claim 1, further comprising directing the polarized gas into a syringe having a plunger that is configured to controllably automatically translate to control the volume of polarized gas received in the syringe to provide a measured amount of polarized gas before the dispensing step.

3. A method according to claim 2, wherein a quantity of nitrogen is also directed into the syringe to a measured volume to define a blended polarized gas mixture.

4. A method according to claim 1, wherein the prepackaged quantity is a partial volume quantity held in a collapsible container.

5. A method according to claim 1, wherein the polarizing, blending, and dispensing steps are carried out at a point of use site.

* * * * *